US011918376B2

United States Patent
Dülk et al.

(10) Patent No.: US 11,918,376 B2
(45) Date of Patent: *Mar. 5, 2024

(54) SUPERLUMINESCENT DIODE MODULE

(71) Applicant: EXALOS AG, Schlieren (CH)

(72) Inventors: Marcus Dülk, Schlieren (CH); Jean Dahdah, Schlieren (CH); Stefan Gloor, Schlieren (CH); Nikolay Primerov, Schlieren (CH); Christian Velez, Schlieren (CH)

(73) Assignee: EXALOS AG, Schlieren (CH)

( * ) Notice: Subject to any disclaimer, the term of this patent is extended or adjusted under 35 U.S.C. 154(b) by 197 days.

This patent is subject to a terminal disclaimer.

(21) Appl. No.: 17/467,348

(22) Filed: Sep. 6, 2021

(65) Prior Publication Data

US 2021/0396922 A1 Dec. 23, 2021

Related U.S. Application Data

(63) Continuation of application No. 16/707,059, filed on Dec. 9, 2019, now Pat. No. 11,131,795.

(30) Foreign Application Priority Data

Dec. 13, 2018 (GB) .................................. 1820370.3

(51) Int. Cl.
*A61B 5/00* (2006.01)
*A61B 1/04* (2006.01)
(Continued)

(52) U.S. Cl.
CPC ............ *A61B 5/6803* (2013.01); *A61B 1/046* (2022.02); *A61B 1/0638* (2013.01); *A61B 3/12* (2013.01);
(Continued)

(58) Field of Classification Search
CPC ..... A61B 5/6803; A61B 1/046; A61B 1/0638; A61B 3/12; A61B 5/0066; A61B 1/0684;
(Continued)

(56) References Cited

U.S. PATENT DOCUMENTS 8,896,842 B2 * 11/2014 Bower .................... A61B 3/102
356/497
9,093,822 B1 7/2015 Chann
(Continued)

FOREIGN PATENT DOCUMENTS

| WO | 2005038418 | 4/2005 |
| WO | 2006039154 | 4/2006 |
| WO | 2014084847 | 6/2014 |

OTHER PUBLICATIONS

Yadid-Pecht et al, "Broadband SLED-based light source (BeST-SLEDTM) and spectrometer," Proc. SPIE 9751, Smart Photonic and Optoelectronic Integrated Circuits XVIII, 97510I (Mar. 3, 2016); doi: 10.1117/12.2213581.

(Continued)

*Primary Examiner* — Mohammed A Hasan
(74) *Attorney, Agent, or Firm* — Nemphos Braue LLC; Michael Antone

(57) ABSTRACT

A module accommodates multiple superluminescent light emitting diodes, SLEDs, 12r, 12g and 12b. The SLEDs are arranged in an enclosure and output respective light beams to propagate into free space within the enclosure. The individual light beams from the SLED sources are combined into a single beam path within the enclosure using beam combiners 40r-g, 40rg-b. Each beam combiner is realized as a planar optical element, the back side of which is arranged to receive a SLED beam and route it through the optical element to the front side where it is combined with another SLED beam that is incident on and reflected by the front (Continued)

side. The free-space propagating combined beam is output from the module via an optical fiber 42 (or through a window).

37 Claims, 14 Drawing Sheets

(51) Int. Cl.
*A61B 1/06* (2006.01)
*A61B 3/12* (2006.01)
*F21V 8/00* (2006.01)
*G02B 27/10* (2006.01)
*G02B 27/12* (2006.01)

(52) U.S. Cl.
CPC .......... *A61B 5/0066* (2013.01); *G02B 6/0006* (2013.01); *G02B 27/1006* (2013.01); *G02B 27/126* (2013.01)

(58) Field of Classification Search
CPC ..... A61B 3/0008; A61B 3/102; A61B 5/0075; G02B 6/0006; G02B 27/1006; G02B 27/126; G02B 6/4214; G02B 6/4268; G02B 6/4286; G01B 9/02007; G01B 9/02091; G01J 3/10; G01J 2003/102; H01L 25/0753
USPC ....................................................... 351/206
See application file for complete search history.

(56) References Cited

U.S. PATENT DOCUMENTS

| | | |
|---|---|---|
| 9,209,605 B1 | 12/2015 | Guo |
| 11,131,795 B2 * | 9/2021 | Dülk .................. A61B 5/6803 |
| 2002/0131049 A1 | 9/2002 | Schmitt |
| 2005/0083533 A1 | 4/2005 | Atia et al. |
| 2006/0072118 A1 | 4/2006 | Chan et al. |
| 2007/0096042 A1 | 5/2007 | Velez et al. |
| 2007/0159639 A1 | 7/2007 | Teramura et al. |
| 2008/0019010 A1 | 1/2008 | Govorkov |
| 2008/0100848 A1 | 5/2008 | Kobayashi |
| 2008/0137180 A1 | 6/2008 | Oh et al. |
| 2008/0272379 A1 | 11/2008 | Laino et al. |
| 2011/0080591 A1 | 4/2011 | Johnson et al. |
| 2012/0162659 A1 | 6/2012 | Goldberg et al. |
| 2012/0257210 A1 | 10/2012 | Whitney et al. |
| 2012/0307512 A1 | 12/2012 | Cogger et al. |
| 2013/0215923 A1 | 8/2013 | Cobb |
| 2014/0153083 A1 | 6/2014 | Hakimi et al. |
| 2014/0180012 A1 | 6/2014 | Yoshino et al. |
| 2016/0000320 A1 | 1/2016 | Sharma et al. |
| 2016/0025298 A1 | 1/2016 | Reitterer |
| 2016/0143520 A1 | 5/2016 | Masaki et al. |
| 2016/0234469 A1 | 8/2016 | Reitterer |
| 2017/0293134 A1 | 10/2017 | Otterstrom et al. |
| 2018/0156596 A1 | 6/2018 | Wang et al. |
| 2018/0252929 A1 | 9/2018 | Tayebati |
| 2019/0121134 A1 | 4/2019 | Pierer |
| 2019/0278096 A1 | 9/2019 | Saracco |
| 2019/0363519 A1 | 11/2019 | Lochman |
| 2020/0110331 A1 | 4/2020 | Reitterer |
| 2020/0158312 A1 | 5/2020 | Dattner |

OTHER PUBLICATIONS

Jain et al, "Compact high power multi-SLED source design and packaging (Conference Presentation)", Proc. SPIE 10085, Components and Packaging for Laser Systems III, 1008507 (Apr. 21, 2017); https://doi.org/10.1117/12.2255766.

Chamorovskiy, SUPERLUM Benchtop Broadband Light Sources 2016. 10.13140/RG.2.1.4779.6086.

* cited by examiner

SUPERLUMINESCENT DIODE MODULE

CROSS-REFERENCE TO RELATED APPLICATIONS

This non-provisional patent application is a continuation application of U.S. patent application Ser. No. 16/707,059, filed Dec. 9, 2019, which claims the benefit of and priority to U.K. Patent Application No. 1820370.3, filed Dec. 13, 2018, each of which is incorporated herein by reference in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

Field of the Invention

The invention relates to broadband optical source modules.

Background

Superluminescent light emitting diodes (SLEDs) are broadband optical sources that find application where semiconductor laser diodes are unsuitable, for example because the coherence of laser light cannot be tolerated or where a broadband emission spectrum is needed.

For some applications where the light properties of a SLED source are in principle suitable, a single SLED cannot be used, since the application requires an emission bandwidth which is broader than a single SLED is capable of delivering. With current technology, a single SLED is capable of emitting over a bandwidth of, for example, at most 50-70 nm in the 800-900 nm wavelength range with sufficient spectral flatness and sufficient output power. In the visible range used for display applications, i.e. in the 450-650 nm wavelength range, a single SLED is capable of emitting over bandwidth of at most 10-30 nm with current technology. Those emission bandwidths are too small for a display or projector application which requires red (~640 nm), green (~520 nm) and blue (~450 nm), i.e. RGB, emission. The emission bandwidth of a single SLED is also too small for certain types of optical coherence tomography (OCT) systems.

FIG. 1 is a schematic drawing of a known SLED source system which is based on using optical fibers with fiber couplers to combine the outputs of two or three SLEDs. The fiber couplers could be fused fiber couplers or fiber-pigtailed free-space filters based on wavelength-division multiplexing (WDM), for example. Modules of this kind have been commercially available from various companies, for example EXALOS (e.g., EBS300080-02 with 140 nm FWHM at 845 nm) or Superlum (e.g., M-D-840-HP with 90-100 nm FWHM at 840 nm).

FIG. 1 shows schematically three SLED source modules in the form of butterfly packages with electrical pins 18 (14 pins being illustrated). The three SLED source modules are labelled 5r, 5g and 5b respectively, to indicate that they house respective SLED sources 12, labelled 12r, 12g and 12b for red, green and blue which output light with centre wavelengths in the red, green and blue visible wavelengths as would be the case for a display source. The source modules 5r/g/b each include an optical fiber pigtail 16 for coupling the light from the SLED source 12 into the end of an optical fiber via a coupling lens 14. The outputs from the upper two SLED modules 5r, 5b are carried by respective optical fibers 20, 22, which lead to a fiber coupler 26 where the two outputs 5r, 5g are combined into a single output fiber 28. The lower SLED source module 5g outputs into an optical fiber 24, which leads to a fiber coupler 30 where it is connected with the optical fiber 28 carrying the outputs from SLED source modules 5r and 5g, so that the output of the fiber coupler 30 has combined all three source outputs in an optical fiber 32.

The design of FIG. 1 is problematic for applications where a polarized output is needed. It is possible to use polarization-maintaining fiber (PMF). However, this is likely to be difficult to implement, since the polarization axis of the SLED output needs to be very well matched to the polarization axis of the PMF if significant losses and unpredictable mode-mixing effects (e.g., polarization crosstalk or polarization mode dispersion (PMD)) are to be avoided. Maintaining the polarization through the fiber couplers would also be technically challenging and may not be possible over large bandwidths, e.g. a few hundred nanometers for a combined beam from three SLEDs of different centre wavelengths.

WO 2006/039154 A1, in FIG. 12 thereof, and US2005/083533 A1, in FIG. 15 thereof, show similar designs of a tunable narrow-band source. The outputs from a bank of five SLEDs each pass through a lens, isolator and further lens. The individual beams then pass through a bank of five tunable Fabry-Perot filters, then each through another lens. The beams are then combined by three mirrors and a beamsplitter and from there fed to an output fiber via two tapping mirrors associated with respective. The disclosed device is a tunable narrow-band source using Fabry-Perot filters as tuning elements.

US2011/080591 A1, in FIG. 5 thereof, discloses a tunable, external cavity laser comprising two semiconductor gain sections and, for tuning, an etalon and respective Fabry-Perot filters. The two beam paths from the two gain sections are combined by mirror and combiner, with the combined beam then being fed to a reflection-mode etalon where unwanted beam components are absorbed. The output is supplied to an optical fiber after the two beams have been combined by a mirror and a combiner. The disclosed device is a tunable narrow-band source using an etalon and Fabry-Perot filters as tuning elements.

SUMMARY OF THE INVENTION

According to a first aspect of the invention there is provided a module for superluminescent light emitting diodes, SLEDs, the module comprising: a housing defining an enclosure of free space; a first SLED source arranged in the enclosure to emit a first SLED beam having a first wavelength range to propagate in the free space along a first beam path; a second SLED source arranged in the enclosure to emit a second SLED beam having a second wavelength range to propagate in the free space along a second beam path; a beam combiner arranged in the enclosure to receive the first SLED beam and the second SLED beam, and to combine them into a combined SLED beam extending in the free space along a combined beam path; and an optical output port arranged to receive light along the combined beam path and to output the light from the housing. The combined SLED beam preferably has a spectrum including the first and second wavelength ranges. The spectrum may be a continuous spectrum covering the first and second wavelength ranges.

In some embodiments, the beam combiner is implemented as a substantially planar optical element. The planar optical element has a front side and a back side, the back side being arranged to receive the first SLED beam at a first angle of incidence and route it through the optical element to the front side and output it from the front side from a first position and in a first direction, and the front side being arranged to receive the second SLED beam at a second position that is coincident with the first position and at a second angle of incidence, and to reflect the second SLED beam into a second direction that is coincident with the first direction. A first lens component may be arranged in the enclosure to act on the first SLED beam and/or a second lens component may be arranged in the enclosure to act on the second SLED beam, e.g. for collimating the SLED output.

A third SLED source may additionally be provided in the module. The third SLED source may be arranged in the enclosure to emit a third SLED beam having a third wavelength range to propagate in the free space along a third beam path. A further beam combiner is then arranged in the enclosure to receive the combined first and second SLED beam and the third SLED beam, and to combine them into a combined beam path extending in the free space.

The combined SLED beam preferably has a spectrum including the first, second and third wavelength ranges. The spectrum may be a continuous spectrum covering the first, second and third wavelength ranges. The optical output port is arranged to receive light along the combined beam path and to output the light along the combined beam from the housing. The further combiner may be implemented as a substantially planar further optical element having a front side and a back side, the back side being arranged to receive the combined first and second SLED beam at a further angle of incidence and route it through the further optical element to the front side and output it from the front side from a further position and in a further direction, and the front side being arranged to receive the third SLED beam at a third position that is coincident with the further position and at a third angle of incidence, and to reflect the third SLED beam into a third direction that is coincident with the further direction. A third lens component may be arranged in the enclosure to act on the third SLED beam.

In embodiments with three or more SLED sources emitting at different wavelength ranges, these may be arranged in order of ascending or descending wavelength range.

In embodiments with descending order, the first wavelength range covers a wavelength range that is longer than the second wavelength range, which is longer than the third wavelength range. Here, an edge filter may be arranged after combining the first SLED beam with the second SLED beam and configured to reject wavelength components that are shorter than the second wavelength range; and a further edge filter arranged after combining the previously combined first and second SLED beams with the third SLED beam and configured to reject wavelength components that are shorter than the third wavelength range. Moreover, a still further edge filter may be arranged in the beam path of the first SLED beam before it is combined with the second SLED beam and configured to reject wavelength components that are shorter than the first wavelength range. These edge filters may be incorporated integrally as coatings on the back side of the beam combiners for example.

In embodiments with ascending order, the first wavelength range covers a wavelength range that is shorter than the second wavelength range, which is shorter than the third wavelength range. Here an edge filter may be arranged after combining the first SLED beam with the second SLED beam and configured to reject wavelength components that are longer than the second wavelength range; and a further edge filter arranged after combining the previously combined first and second SLED beams with the third SLED beam and configured to reject wavelength components that are longer than the third wavelength range. Moreover, a still further edge filter arranged in the beam path of the first SLED beam before it is combined with the second SLED beam and configured to reject wavelength components that are longer than the first wavelength range. These edge filters may be incorporated integrally as coatings on the back side of the beam combiners for example.

In some embodiments, one or more beam-shaping components are arranged in the enclosure. Beam-shaping components may be provided for any one of the SLED beams, or all of them, or any other permutation. The beam-shaping components may act to transform a collimated SLED beam from an elliptical beam shape into a circular beam shape. Beam-shaping components may also be provided for the combined beam. Moreover, an aperture may be arranged in the combined beam path, e.g. to clean up the combined beam characteristics and filter out stray light that may be present in the enclosure.

The module may further comprise a substrate arranged in the enclosure and having mounted thereon at least the SLED sources and the beam combiner(s) as well as optionally any other ones of the components as desired.

As well as SLEDs, the module may accommodate a laser diode, with the laser diode's beam also being combined into the SLED beams. Namely, the module may further comprise: a laser diode source arranged in the enclosure to emit a laser beam to propagate in the free space; and a further beam combiner arranged in the enclosure to combine the laser beam with at least one of the SLED beams (first, second or combined) to propagate along the combined beam path. Another design alternative is to provide a module comprising: a housing forming a free-space enclosure; at least a first SLED source arranged in the enclosure to emit a first SLED beam having a first wavelength range to propagate in the free space; a laser diode source arranged in the enclosure to emit a laser beam to propagate in the free space; and a beam combiner arranged in the enclosure to combine the laser beam with at least one of the first SLED beam and the second SLED beam into the combined beam path. With reference to the above discussion of edge filters, when the module includes a laser diode, the laser diode may be arranged in the cascade of ascending or descending wavelength at the appropriate position and with an associated edge filter.

In some embodiments, the optical output port comprises: an optical fiber coupler which is attached to an optical fiber and arranged to couple the combined beam (SLED only or SLED and LD) into an end of an optical fiber to allow the combined beam to output from the housing via the optical fiber. In other embodiments, the optical output port comprises: a window arranged in the housing to allow the combined beam (SLED only or SLED and LD) to output from the housing.

Various arrangements of the SLEDs are possible within the enclosure. The enclosure may for example be substantially rectangular in plan view, as is the case for a butterfly package. The optical output port may be arranged at one end of the enclosure in an end wall of the housing. In one arrangement, each of the SLED sources is arranged on the same side of the enclosure so as to emit their beams substantially in the same direction across the enclosure.

In an other arrangement, one of the SLED sources is arranged on one side of the enclosure and another of the SLED sources is arranged on the other side of the enclosure so that they emit their beams in substantially opposed directions across the enclosure. In a still further arrangement, one of the SLED sources is arranged on one side of the enclosure and another of the SLED sources is arranged at an end of the enclosure opposite the end that accommodates the optical output port so that they emit their beams in substantially orthogonal directions across and along the enclosure respectively.

SLED modules embodying the invention are suited to incorporation into a number of systems, such as the following.

There may be provided an optical coherence tomography system, comprising: a module according to an embodiment of the invention; and a beam splitter arranged to receive light output from the source module and to direct one component into a first, sample arm to a sample position and another component to a second, reference arm, and to recombine light received back from the first and second arms and direct the recombined light to a detector.

There may be provided a fundus imaging system, comprising: a module according to an embodiment of the invention; and an optical arrangement configured to direct light output from the source module to a sample position and collect light received back from the sample position into a fundus imaging unit.

There may be provided an endoscopic imaging system, comprising: a module according to an embodiment of the invention arranged to direct its output beam into a light guide; and an insertion tube adapted for insertion into a bodily orifice in which is arranged at least a part of the light guide, wherein the light guide terminates proximal a distal end of the insertion tube.

Generally, the number of beam combiners that are needed will be one fewer than the number of beams to be combined.

BRIEF DESCRIPTION OF THE DRAWINGS

This invention will now be further described, by way of example only, with reference to the accompanying drawings.

DETAILED DESCRIPTION

Figure 1:
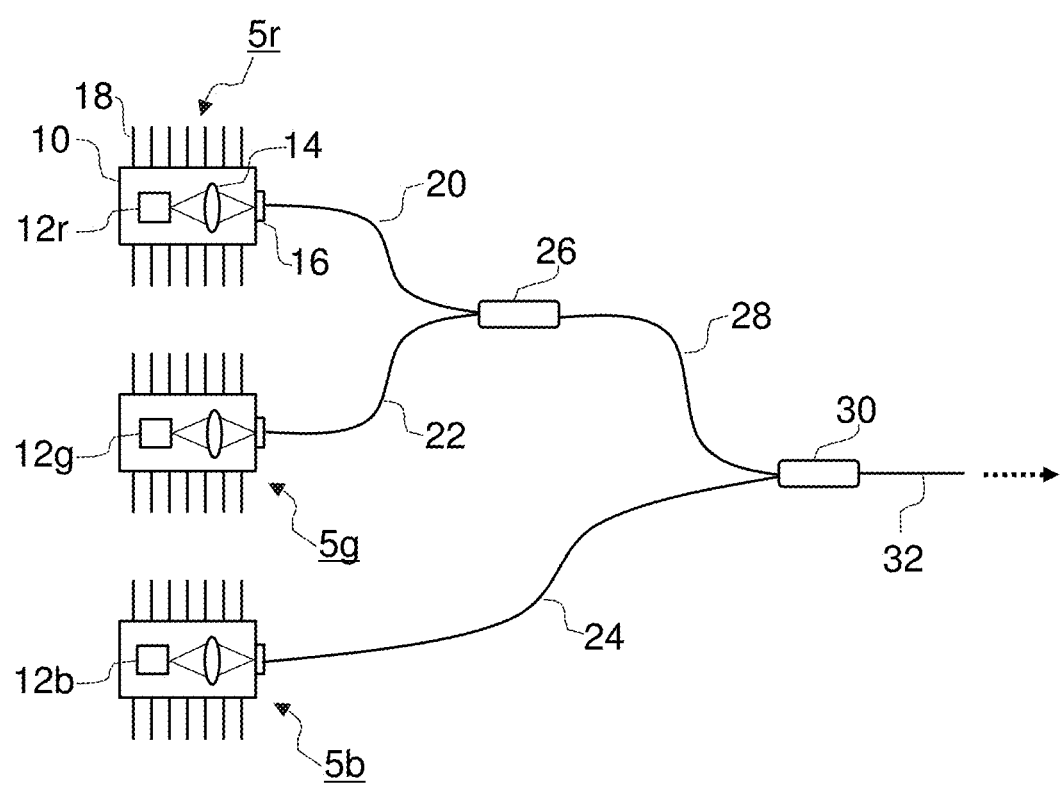
FIG. 1 is a schematic drawing of a known SLED source system.

In the following detailed description, for purposes of explanation and not limitation, specific details are set forth in order to provide a better understanding of the present disclosure. It will be apparent to one skilled in the art that the present disclosure may be practiced in other embodiments that depart from these specific details.

The wavelength range of an individual SLED emitter is defined by a variety of design parameters including its epitaxial semiconductor stack structure and materials, the dimensions of the ridge in the case of a ridge structure, and the properties of the chip's end facets. The wavelength range may have a value between 3 nm and 160 nm at full width half maximum (FWHM), i.e. 3 dB attenuation level. It is the case that, for comparable designs, the FWHM scales with the square of wavelength, so the maximum possible wavelength range for comparable designs increases for longer wavelengths. With future developments in technology it may be possible to broaden the maximum wavelength range at any particular center wavelength. The wavelength range covered by an individual SLED emitter as disclosed herein may have any value between 3 nm and 160 nm. With current technology and using the arsenide- and phosphide-based materials system wavelength ranges up to about 160 nm are achievable in SLEDs with center wavelengths in the near infrared (NIR) and infrared (IR). With current technology and using the nitride-based materials system wavelength ranges up to 30 nm are achievable in blue and green SLEDs. For example, the wavelength range may have a value of 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 110, 120, 130, 140 or 150 nm.

To suppress lasing in edge-emitting ridge SLED structures, as is known in the art, one or more of the following measures can be undertaken:

(i) the ridge may extend such that its optical path intersects with the chip's front (output) facet at a non-normal angle, either by the ridge being straight and extending at a non-normal angle to the parallel planes of the chip's front and back facets, or by having a curved portion adjacent the front facet;

(ii) absorber materials may be provided adjacent the back facet which are absorbent over the SLEDs amplification wavelength range;

(iii) the ridge may terminate part way between the front and back facets, e.g. at a tilt angle so that reflections from the back facet are inhibited from coupling back into the waveguide; and (iv) the front and/or back facets may be coated with anti-reflection coatings.

In the following detailed description, the repeated references to red, green and blue wavelength ranges, are specific labels that make the description of the examples convenient to understand. While these colors are technically significant for display and projection applications, it will be understood that they may be generalized to mean first, second and third different emission wavelength bands from first, second and third SLEDs. Moreover, one or more of these bands need not be in the visible region, since for example one or more of the bands may be in the near infrared, or near ultraviolet.

Figure 2:
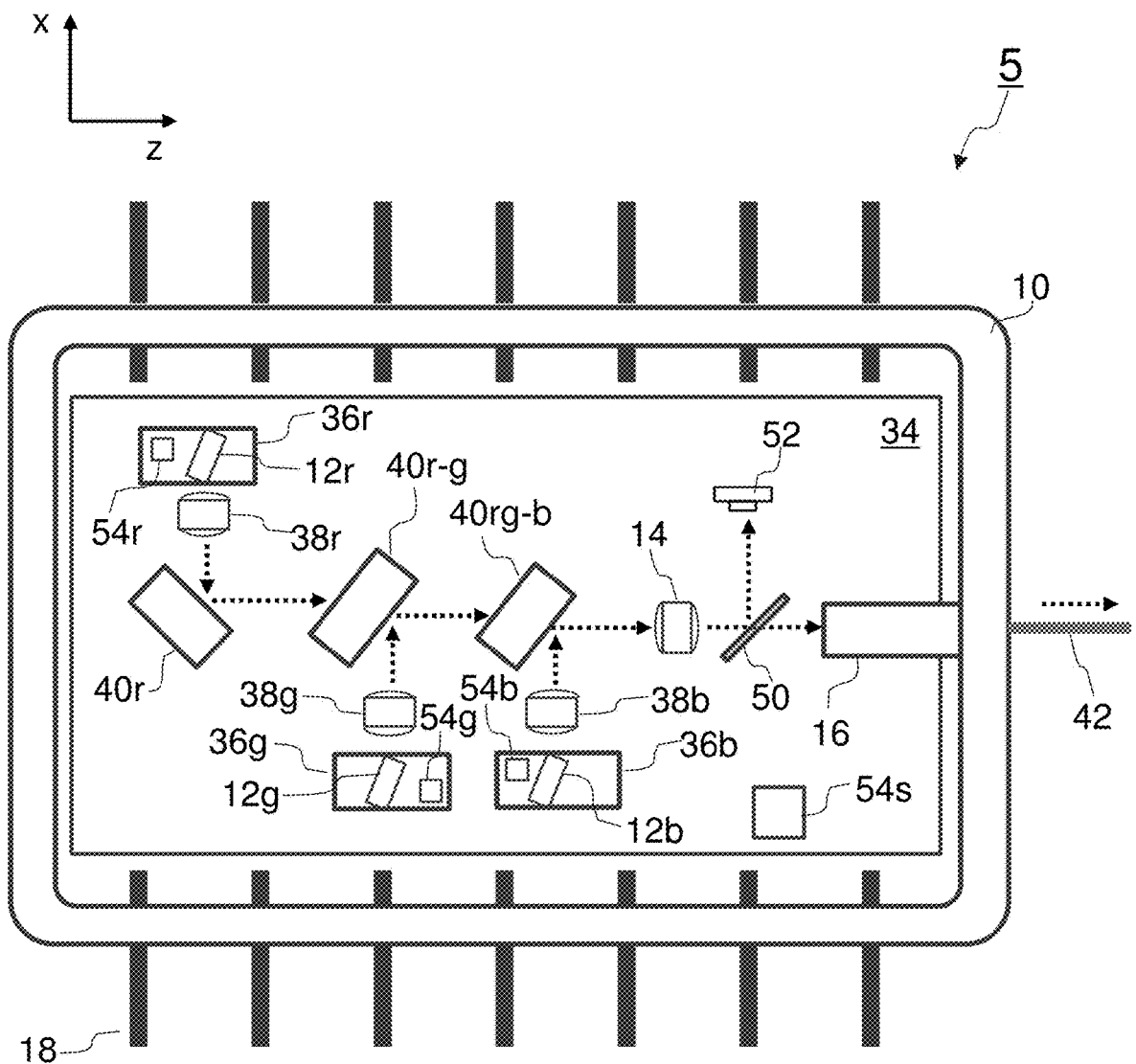
FIG. 2 is a schematic plan view of a SLED source module according to a first embodiment with an optical fiber output.

FIG. 2 is a schematic plan view of a SLED source module according to a first embodiment with an optical fiber output. The SLED module is based on a butterfly package 5, shown as a 14-pin butterfly package. The butterfly package 5 has a plurality of terminal pins 18 via which electrical connections may be made to components housed in the package. The butterfly package 5 has a housing 10 that forms an enclosure in which the SLEDs are accommodated as well as associated components. The components are at least for the most part mounted directly or indirectly on a main board 34, which may also be referred to as a carrier board, substrate, optical breadboard or mounting board. The main board 34 is provided with a temperature sensor 54s arranged on the main board to measure the temperature of the main board. The main board 34 should have good thermal conductivity for heat dissipation, and should be mechanically stiff. Suitable materials choices are ceramic, e.g. AlN or Al2O3, a suitable metal, e.g. copper, aluminium or alloys containing either or both of these metals such as CuW. The upper and/or lower surface of the main board 34 may be metallized to support solder processes for the attachment of the components, in particular for electrical connections. Metallization may also aid good thermal connection to cooling elements for maintaining the temperature inside the enclosure within a specified range. For physical attachment of components by bonding, e.g. with epoxy resin, the upper and/or lower surfaces of the main board 34, or selected areas thereof, may be specified with a minimum surface roughness to provide good adhesion.

The housing 10 and the enclosure it defines by its internal walls are substantially rectangular in plan view as illustrated aligned with orthogonal axes x and z respectively across and along the module as illustrated, with y being the axis out of the paper, i.e. the vertical. The SLED module has its optical output port arranged at one end of the enclosure in an end wall of the housing 10. The optical output port in this embodiment is realized with optical fiber in the form of an optical fiber ferrule 16, which is attached to an optical fiber 42 that may be single mode or multimode and may be polarization maintaining (or not) as desired. The ferrule 16 and fiber 42 form a so-called pigtail and serve to couple the combined beam from the different SLEDs 12 into the end of the optical fiber and thus out of the module 5. The fiber ferrule 16 may also be attached to the main board 34, or may be secured to the housing 10, e.g. to the end wall. It will be appreciated that the module also has a lid (not shown) which may be secured removably or non-removably to the housing by fasteners, such as screws or rivets, and/or adhesive bonding, welding or other fastening or sealing means as desired.

The components include first, second and third SLED sources 12r, 12g and 12b. The SLEDs 12 are arranged in the enclosure to emit respective first, second and third beams having first, second and third wavelength ranges into free space within the enclosure along first, second and third beam paths. The three wavelength ranges are labelled as 'r', 'g' and 'b' to indicate red, green and blue wavelength ranges by way of example, and also to provide intuitive labelling. These could however equally well be three wavelength ranges in some other part of the visible, near-UV or near-infrared (NIR). The SLEDs 12 are mounted on respective submounts 36, labelled 36r for the red SLED 12r, 36g for the green SLED 12g, and 36b for the blue SLED 12b. The submounts 36 are in turn mounted on the main board 34. The materials choices for the submounting boards 36 are similar to those as described above for the main board 34. The mode of assembly with populated submounts on a main board is referred to as a chip-on-submount (CoS) in the art. The SLED chips 12 are schematically shown mounted at an angle to their submounts 36 and the sides of the rectangular enclosure as would be the case for tilted, single-pass SLEDs in which the ridge waveguide of the SLED is tilted as a way of hindering reflections from the chip end facets, in particular the back facet, coupling back into the ridge waveguide, thereby to suppress lasing action. Typically, the reflectivity of both chip end facets is kept as low as possible, and the light is amplified along the waveguide on a single pass. The ridge and hence the underlying waveguide W may be straight or incorporate a curved portion. Back-reflection may be further suppressed by introducing a passive absorber section in the SLED chip. The choice of SLED type is flexible, e.g. double-pass designs with the back facet having a high reflectivity could be used. The submounts 36 may also have respective temperature sensors 54 mounted on them, labelled 54r for the red SLED submount 36r, 54g for the green SLED submount 36g, and 54b for the blue SLED submount 36b. These temperature sensors allow the temperature local to each SLED to be monitored. The temperature sensors 54s, 54r/g/b may have their signals used as control inputs for one or more cooling elements (not shown). For example the mounting board 34 may have attached to its upper or lower surface a thermoelectric cooler, e.g. a Peltier device. The submounts 36r/g/b may also have individual cooling elements (not shown) that can be independently controlled via the respective temperature measurements from sensors 54/r/g/b.

The SLED output beams from the SLEDs 12r/g/b are collimated by respective collimating lenses 38r/g/b The red SLED 12r is arranged on one side of the enclosure and the green and blue SLEDs 12g, 12b are arranged on the other side of the enclosure so that the red beam propagates initially in the opposite direction to the blue and green beams laterally across the enclosure, i.e. in negative-x and positive-x directions respectively. The red SLED beam after collimation by lens 38r is deflected through 90 degrees from the negative-x direction into the z-direction by a mirror 40r arranged at 45 degrees to x and z. The z-travelling red beam is incident on the back face of a beam combiner 40r-g which has the function of combining the red beam with the green beam. The beam combiner 40r-g is a planar optical element which is made of a suitable glass or crystal material. The beam combiner 40r-g has a front side and a back side. The red beam is incident on the back side of the beam combiner 40r-g at an angle of incidence which causes the beam to refract into the beam combiner 40r-g. The back side is preferably coated with an antireflection coating (ARC) that is effective for the wavelength range, angle of incidence and polarization state of the red beam. The red beam is then routed through the glass or crystal to the front side and is once more refracted as it outputs from the front side. The front side of the beam combiner 40r-g is arranged to receive the green beam propagating in the positive-x direction from the collimating lens 38g at a position on the front surface that is the same as where the red beam passes through the front surface. Moreover, the beam combiner 40r-g is configured and arranged so that the green beam reflected from its front surface propagates in the same direction as the red beam output from the front surface, preferably the z-direction as schematically illustrated. The red and green beams thus emerge from the beam combiner 40r-g as a combined beam propagating in free space within the enclosure in direction z. The beam combiner 40r-g will usually be planar, but if desired it could be slightly curved, but still substantially planar, to provide some focusing or defocusing of one or more of the red and green beams.

The combined red and green beam is then combined with the blue beam in a similar way using a further beam combiner labelled 40rg-b. Namely, the blue beam output from the blue SLED 12b travelling in the positive x-direction is collimated by collimating lens 38b and is incident on the front surface of the beam combiner 40rg-b, and the back surface of the beam combiner 40rg-b receives the combined red-green beam. The red, blue and green beams thus emerge from the beam combiner 40rg-b as a combined beam propagating in free space within the enclosure along an optical path in direction z.

The combined beam is focused onto the end face of the optical fiber 42 held in the pigtail ferrule 16 by a coupling lens 14. In addition, to measure the power of the combined beam, a tapping mirror 50 is arranged in the combined beam, e.g. between the coupling lens 14 and fiber coupler 16 as illustrated, to tap off a small part of the beam to a power monitor 52, which may be realized as a photodiode, for example. The tapping mirror 50 may for example be a planar piece of clear glass, i.e. glass that is transparent over the combined wavelength range of the three components of the combined beam, so that a few percent of the combined beam, e.g. 1-5% of its power, is reflected away into the power monitor by residual reflection. Alternatively, a tap mirror could be omitted, and the power monitor could face the point where the combined beam is focused onto the fiber end and monitor power through monitoring back-scattered light from the fiber end.

Other design options may be incorporated into the module. For example, edge filters may be incorporated to filter each of the beams prior to them being combined, so as to filter out wavelengths that are outside the wavelength range of each SLED. In the case that the beams are combined in order of decreasing wavelength, with the shortest wavelength being combined last, as is the case of the embodiment of FIG. 2 where the combination order is red then green then blue, then each edge filter will cut-off wavelengths shorter than the intended wavelength range of each SLED. For example, in the embodiment of FIG. 2, if the red SLED is intended to output over a range 700-750 nm, then a suitable edge filter may reject wavelengths less than 700 nm, or some other value close to 700 nm, such as 690, 680, 670 nm etc. as desired. Alternatively, if the beams are combined in order of increasing wavelength, with the longest wavelength being combined last, e.g. a combination order of blue then green then red, then each edge filter will cut-off wavelengths longer than the intended wavelength range of each SLED. Edge filters may be incorporated integrally into the front side of the mirror 40r and the front and/or back sides of the beam combiners 40r-g, 40rg-b as coatings. Alternatively, edge filters may be added as separate components and mounted on the main board 34. Band filters could also be used for filtering out unwanted wavelengths in addition to, or instead of edge filters.

Another design option is to use a polarization filter on the combined beam, e.g. prior to or after the coupling lens 14, to increase the polarization extinction ratio (PER) of the outputted beam. This may be useful when the module is specified to have a high PER, e.g. at least 20-30 dB, whereas the intrinsic PER of one or more of the SLEDs 12 may be lower, e.g. only 3-10 dB.

It will be understood that references to a combined beam could be taken to imply that the different SLEDs are simultaneously emitting. However, this is not necessarily the case. For a display or projection application, red, green and blue beams will generally be emitting simultaneously (unless the image is exceptionally only red etc.). However, for other applications, the different SLEDs may be driven selectively and not all be active at the same time. For example, if the module is intended for a multi-modality system requiring say one group of one or more SLEDs to emit in the NIR for OCT and another group of one or more SLEDs to emit in the visible for fundus imaging, then these two groups would not generally be operated simultaneously, but these two groups are nevertheless arranged in the module to have a combined beam path, i.e. so that their beams are (or would be) combined when (or if) they are simultaneously emitted.

Figure 3:
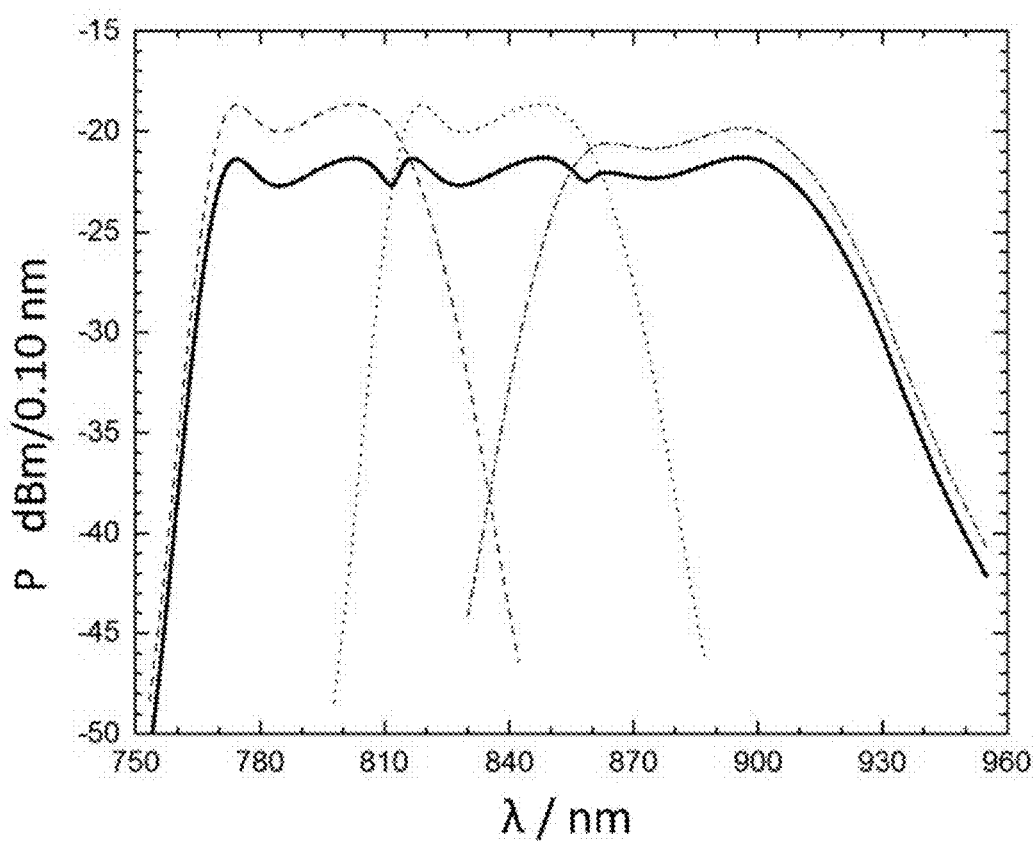
FIGS. 3 and 4 are graphs of output power as a function of wavelength for a SLED source module according to the first embodiment.

FIG. 3 is a graph of output power, P, on a logarithmic scale of arbitrary units, as a function of wavelength, A, in nanometres for an example SLED source module according to the first embodiment which provides a continuous spectrum in the NIR in the range of about 760-950 nm. The spectrum of the combined beam is shown with the solid line, and the spectra from the individual SLEDs with the dashed, dotted and chain-dotted lines.

Figure 4:
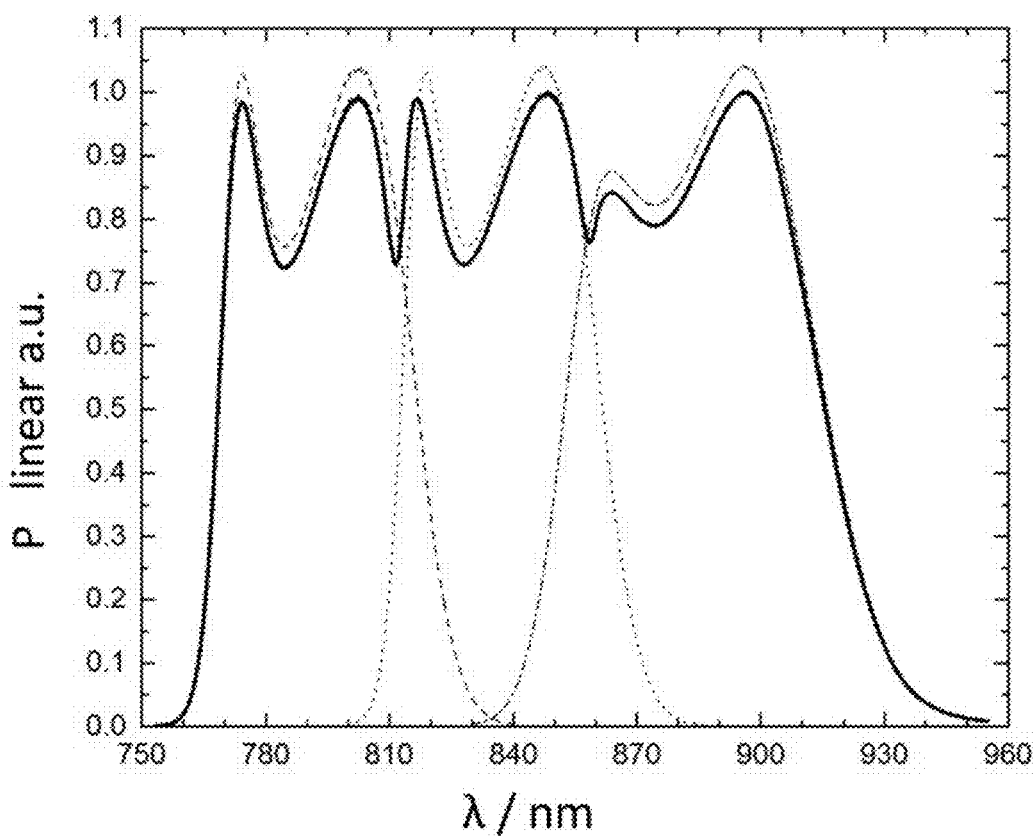

FIG. 4 is a graph of output power, P, on a linear scale of arbitrary units, as a function of wavelength, A, in nanometres for the same results as shown in FIG. 3. In other words, FIG. 4 is merely a different presentation in the y-axis of the same results as shown in FIG. 3.

The redmost SLED (dashed line) has a centre wavelength of ~790 nm and a bandwidth of 45-50 nm, the middle SLED (dotted line) has a centre wavelength of ~840 nm and a bandwidth of 50-55 nm, and the infraredmost SLED (dashed-dotted line) has a centre wavelength of ~880 nm and a bandwidth of 55-60 nm. The specification of the SLED source module's output is: centre wavelength of 845 nm, 3 dB bandwidth of 145 nm, 10 dB bandwidth of 165 nm, 10 dB wavelength range of 765-930 nm, 10 mW output power and a coherence length of 2.9 micrometres. It will be appreciated this output is from the red end of the visible to near-infrared, which is suitable for OCT systems. With other SLED sources currently available, other wavelength ranges can be covered, e.g. spanning the visible range, such as needed for RGB displays, and ranges further into the near-infrared. It is expected that improved specifications will become available with the present designs as SLED sources continue to improve their performance.

Figure 5:
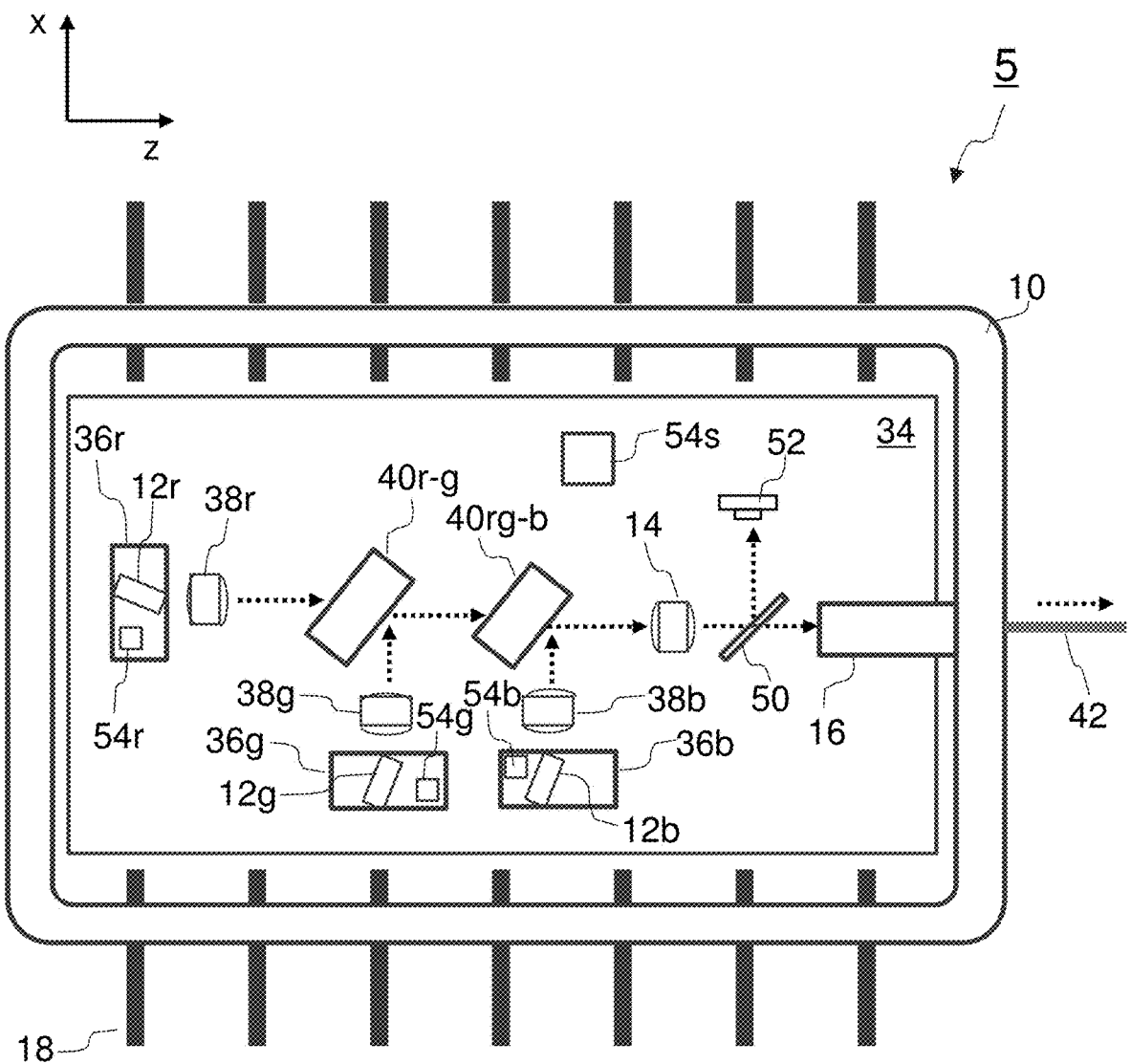
FIG. 5 is a schematic plan view of a SLED source module according to a second embodiment with an optical fiber output.

FIG. 5 is a schematic plan view of a SLED source module according to a second embodiment with an optical fiber output. The embodiment of FIG. 5 only differs from that of FIG. 2 in that the mirror 40r of FIG. 2 is omitted, since the red SLED source 12r is arranged to emit along the enclosure in the z-direction and directly project onto the back face of the beam combiner 40r-g via the collimating lens 38r.

Figure 6:
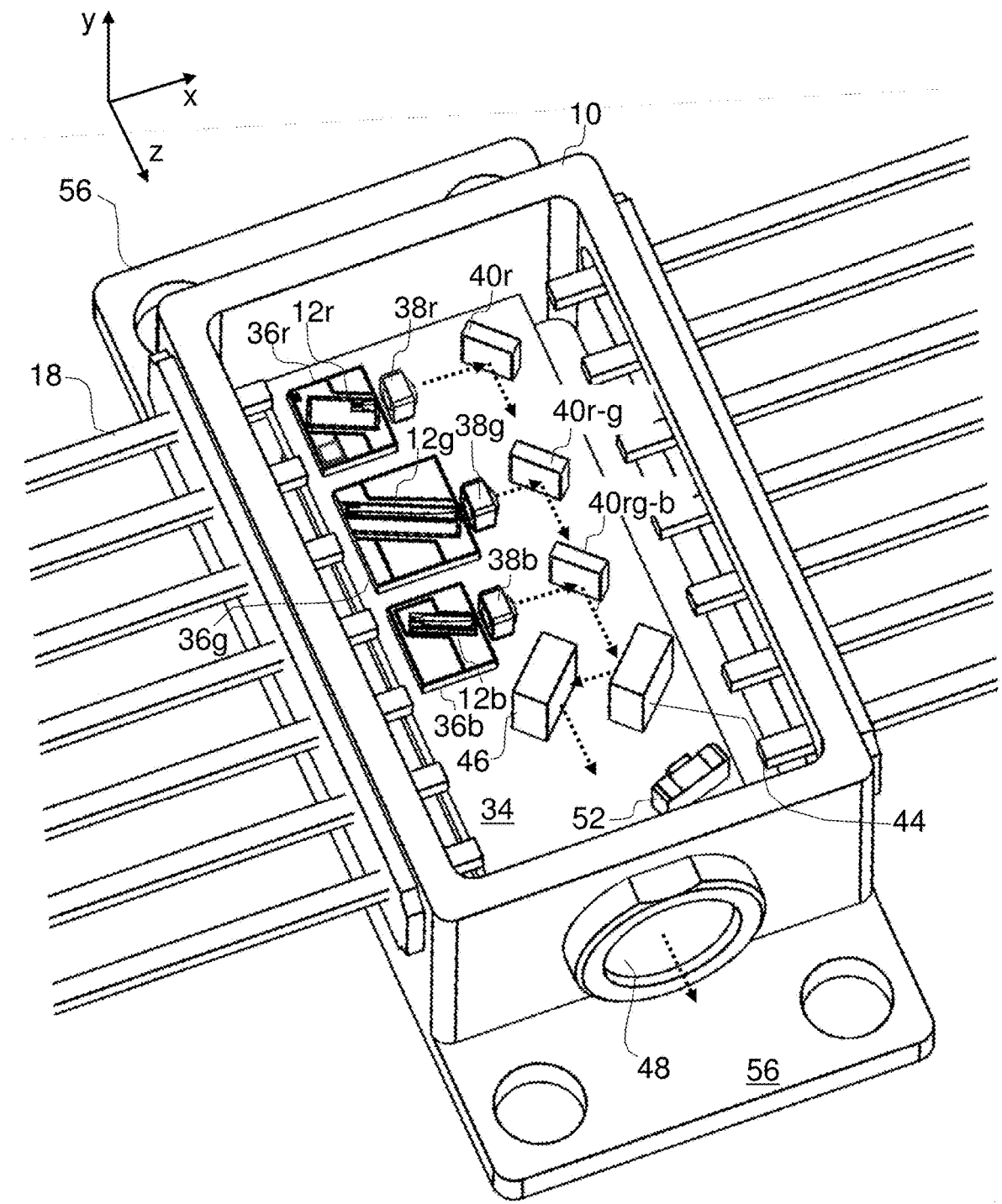
FIG. 6 is a schematic perspective view of a SLED source module according to a third embodiment with a free-space output.

FIG. 6 is a schematic perspective view of a SLED source module according to a third embodiment with a free-space output. The optical output port comprises a window 48 arranged in the end wall of the housing 10 to allow the combined beam to be output from the housing in the z-direction. Compared with FIGS. 2 and 5 with optical fiber output, there is no requirement for a focusing lens 14 in the embodiment of FIG. 6, so this is omitted from the drawing. However, optionally, a lens in the same position as lens 14 of FIGS. 2 and 5 could be included in the embodiment of FIG. 6, but this need not be for creating a focus within the enclosure, but rather more likely would be provided to bring the output light beam to a defined focus some specified distance away from the module, or for providing an auxiliary or supplementary collimating function for the combined beam additional to that provided by the individual collimating lenses 38. Also visible in FIG. 6 are the end flanges 56 of the butterfly package 5, which are also present in the embodiments of FIGS. 2 and 5, although not illustrated. Moreover, compared with FIG. 2 and also FIG. 5, it can be seen that in FIG. 6 all three SLED sources 12 on their respective boards 36 are arranged on the same side of the enclosure all emitting in the same direction across the enclosure, so that compared with FIG. 2 mirror 40r is aligned with similar rotation to the planar beam combiners 40r-g and 40rg-b. This arrangement results in the combined first, second and third output beams being closer to the sidewall of the housing 10, so that two beam offset mirrors 44, 46 are provided for bringing the combined output beam away from the sidewall and back to a more central position aligned with the centre of the output window. The power monitor 52 is arranged to receive a small power component, e.g. 1-3%, of the combined output beam that is transmitted through the first beam offset mirror 44, i.e. is arranged 'behind' the beam offset mirror 44. For this purpose, the first beam offset mirror 44 may be designed with a reflectivity to the combined beam of slightly less than 100%. The power monitor 52 could instead be arranged behind the second beam offset mirror 46. The beam offset mirrors 44, 46 are attached to the mounting board 34. The beam offset mirrors 44, 46 will in the normal case be planar, but they could be made concave or convex if desired to provide some focusing, collimating or defocusing effect. It will be appreciated that this arrangement with all the SLED sources 12 arranged on the same side of the enclosure is also available with optical fiber output, i.e. in conjunction with a fiber ferrule 16 and optical fiber 42 as shown in FIGS. 2 and 5.

Figure 7:
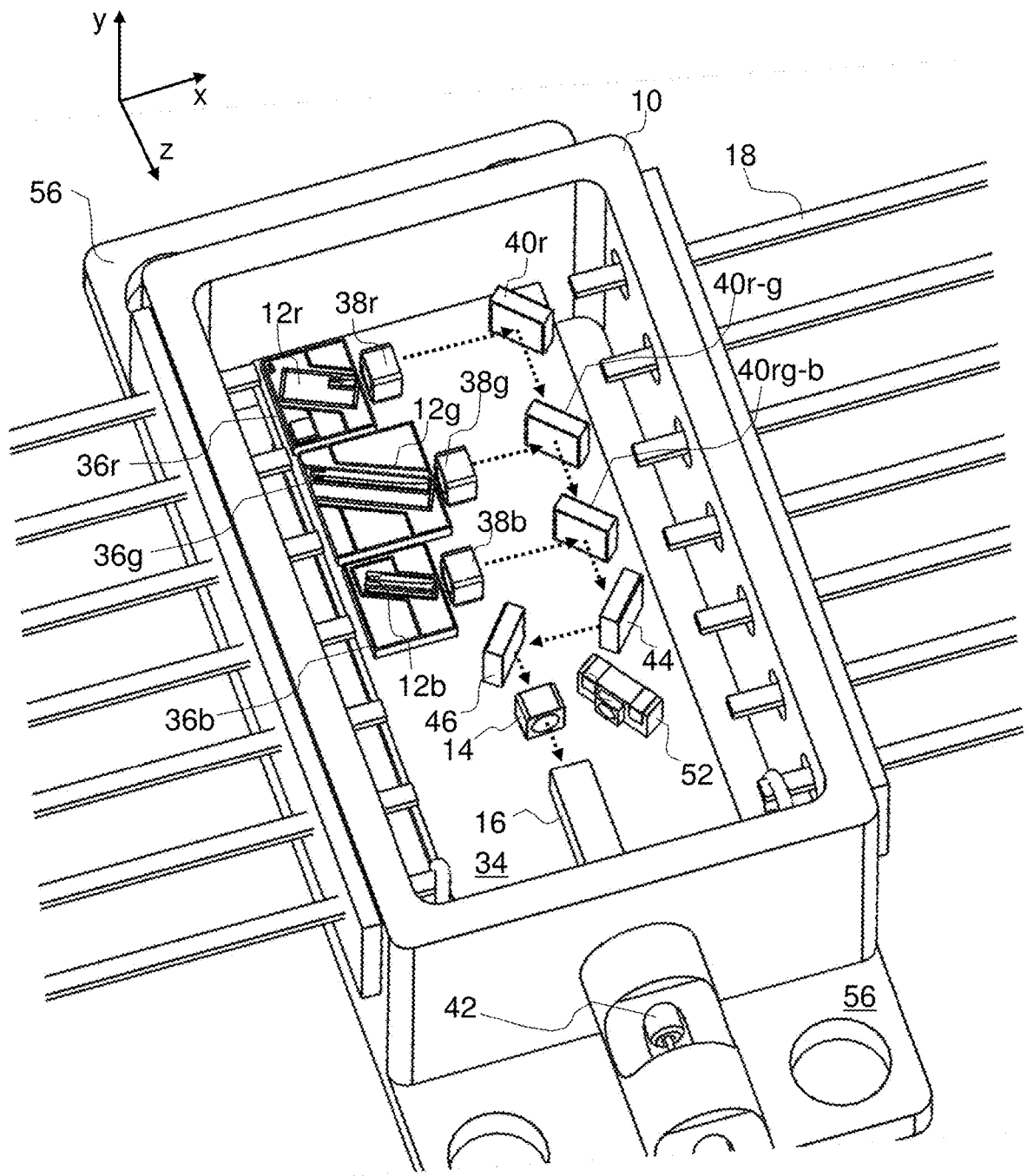
FIG. 7 is a schematic perspective view of a SLED source module according to a fourth embodiment with an optical fiber output.

FIG. 7 is a schematic perspective view of a SLED source module according to a fourth embodiment with visible, RGB-SLEDs and an optical fiber output. The design corresponds to that of FIG. 6, except that instead of a window 48, there is an optical fiber ferrule 16 and optical fiber 42 forming a pigtail arrangement, as in the embodiments of FIG. 2 and FIG. 5 with the power monitor 52 facing the fiber end where the combined SLED beams are focused by coupling lens 14.

In the above embodiments, attachment of the components to the main board 34, the submounts 36 and the housing 10 may be by UV-curable epoxy resin. The attachment is done with high accuracy placement. Active alignment, i.e. with the SLED sources switched on during alignment, may be used during the component attachment to ensure that the different optical components are correctly located for guiding and combining the different beams as desired. Active alignment may also help ensure efficient coupling into an output fiber or that a free-space beam has the desired output direction, position and focal properties (e.g. is precisely collimated or with a focus at a specified distance from the module). After UV-curing of the epoxy resin, the main board 34 with its attached components may be baked in an oven. It will be appreciated the components 14, 38, 40 etc. may not be single components as illustrated, but may each consist of two or more components, such as isolators (electrical, thermal and/or vibration), and submounts. Moreover, physically separate filters, polarizers, apertures or other optical components (not illustrated) may also be included that are attached to the mounting board 34.

Figure 8:
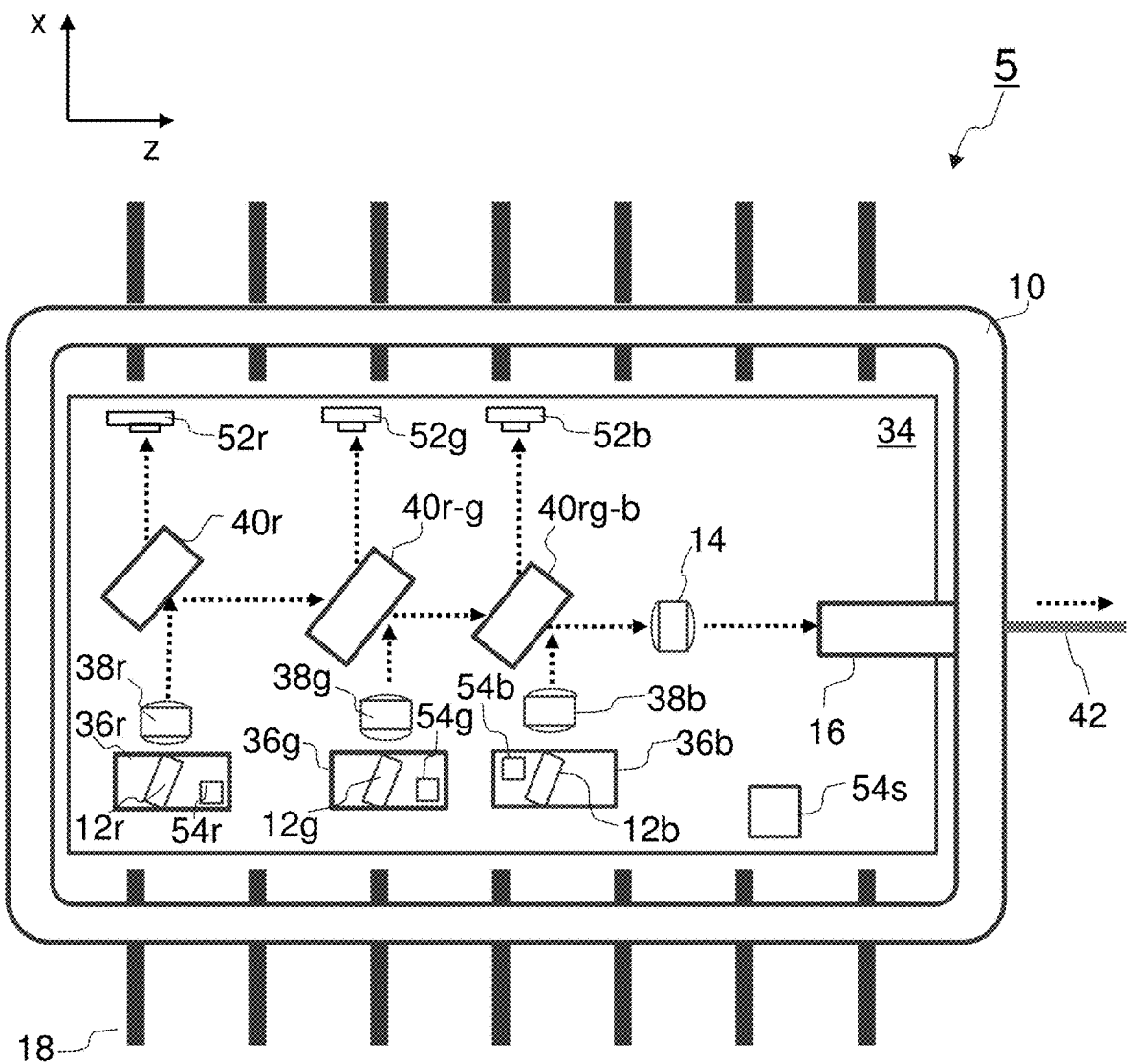
FIG. 8 is a schematic plan view of a SLED source module according to a fifth embodiment with individual power monitors for each SLED.

FIG. 8 is a schematic plan view of a SLED source module according to a fifth embodiment. The design of FIG. 8 is similar to that of FIG. 6, but differs in that individual power monitors 52r/g/b are provided for each of the SLEDs 12r/g/b respectively (instead of having one power monitor 52 for the combined RGB beam). Each individual power monitor 52 is arranged to receive a small fraction of the light power that has been transmitted through the deflecting mirror or beam combiner 40, these being configured to have slightly less than 100% reflection to the SLED beam, so that a small power fraction, e.g. 1-3%, of the SLED beam passes through the element 40 to the power monitor 52. Other options for arranging the power monitors are possible. For example, the individual power monitors could be arranged adjacent the back facet of each SLED in order to measure the light that 'leaks', i.e. is emitted, from the back facet of the SLED. Having power monitors for each SLED may be useful in a number of applications. For example, it may be useful when the output needs to meet particular safety standards, and those safety standards specify different safety limits for different ones of the wavelength ranges output by the SLEDs. The outputs from the power monitors would then be supplied to a controller that would control the drive currents of each SLED so that the output power from each SLED did not exceed an upper limit. For example, in laser class 1, the safety limit for blue light is approximately an order of magnitude lower than for green and red light. Having individual power monitors for each SLED may also be beneficial in projector or display applications where true color is important, since these can be used to maintain the correct color balance via feedback to a controller which controls the SLED drive currents accordingly. Having individual power monitors for each SLED may be particularly beneficial when the package is not under tight environmental control, e.g. when the package has no or limited temperature control features, such as temperature sensors (thermometers) and cooling devices. A further level of sophistication would be where the power monitors are adapted to detect also spectral information, i.e. power as a function of wavelength. For example, a dual-photodiode detector could be employed as the element 52, where the two photodiodes have different spectral response curves (e.g., by means of a spectral filter placed on top of the photosensitive area) to allow monitoring power changes on a wavelength-dependent basis.

Figure 9:
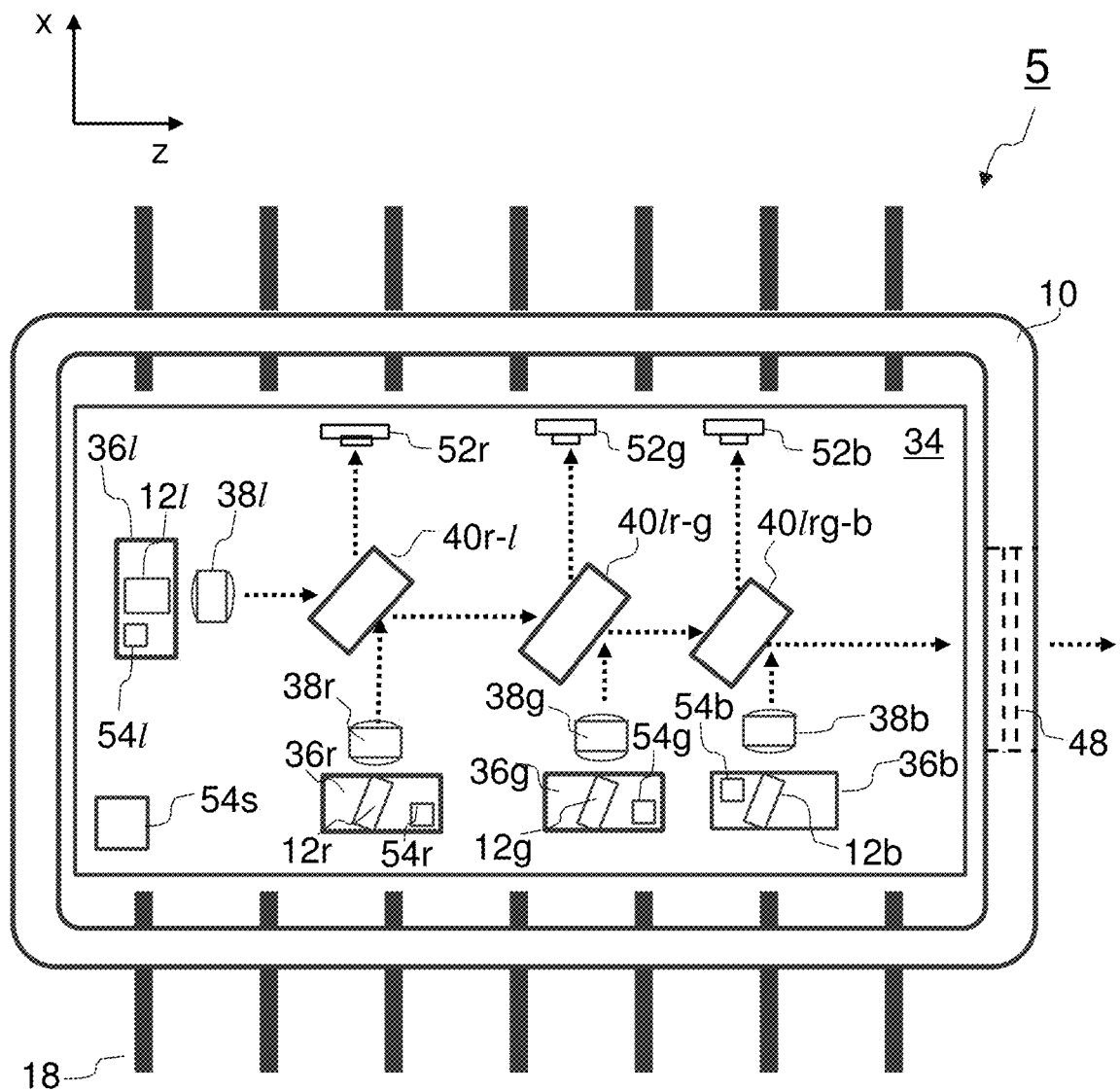
FIG. 9 is a schematic plan view of a source module according to a sixth embodiment combining multiple SLEDs and a laser diode (LD).

FIG. 9 is a schematic plan view of a source module according to a sixth embodiment combining multiple SLEDs and a laser diode, i.e. a combined SLED and LD module. The design of FIG. 9 may be considered to combine the three SLEDs and associated components of the design of FIG. 8 with a laser diode source 121 which is arranged in an analogous position to the red emitter of FIG. 5 to emit along the enclosure in the z-direction and directly project onto the back face of a beam combiner 401r-g via a collimating lens 381. In this way, the laser beam output from the laser diode 121 is combined and colinearly aligned with the combined SLED output beam to form a single output beam path, i.e. an output with a common optical axis. The laser diode 121 may be an edge emitting laser, or a vertical cavity surface emitting laser. As an aside, it is noted that the illustrated module has free-space output via a window 48, but a variant with fiber output as in FIG. 8 is also possible. Practical uses of a module according to this embodiment may include use as a source for an ophthalmic instrument. An embodiment may include two or three SLEDs arranged to provide a common output as a combined beam for one modality, as well as a laser diode for another modality. For example, there could be a group of three RGB SLEDs for color fundus imaging as well as a laser diode with an output at 488 nm for dye excitation in fluorescence imaging, or spectroscopy, all accommodated in the same package. Another useful application may be a module with a plurality of SLEDs to provide a combined beam for OCT in combination with a laser diode for surgery, e.g. micro-vascular surgery in the retina. OCT measurements could thus be integrated with the surgical intervention. Further variants of this embodiment would be to accommodate a second or still further laser diodes in addition to the plurality of two or more SLED sources, or another group of SLEDs, e.g. to have an NIR group and an RGB group. The module may thus include SLED sources, or a mixture of SLED and LD sources, that are associated with different modalities. Each modality may require a single SLED or laser diode source, or a group of two or more SLED or laser diode sources. Modules according to embodiments of the invention may thus provide a single package for multi-modality applications, e.g. two, three, four or more different modalities.

Figure 10:
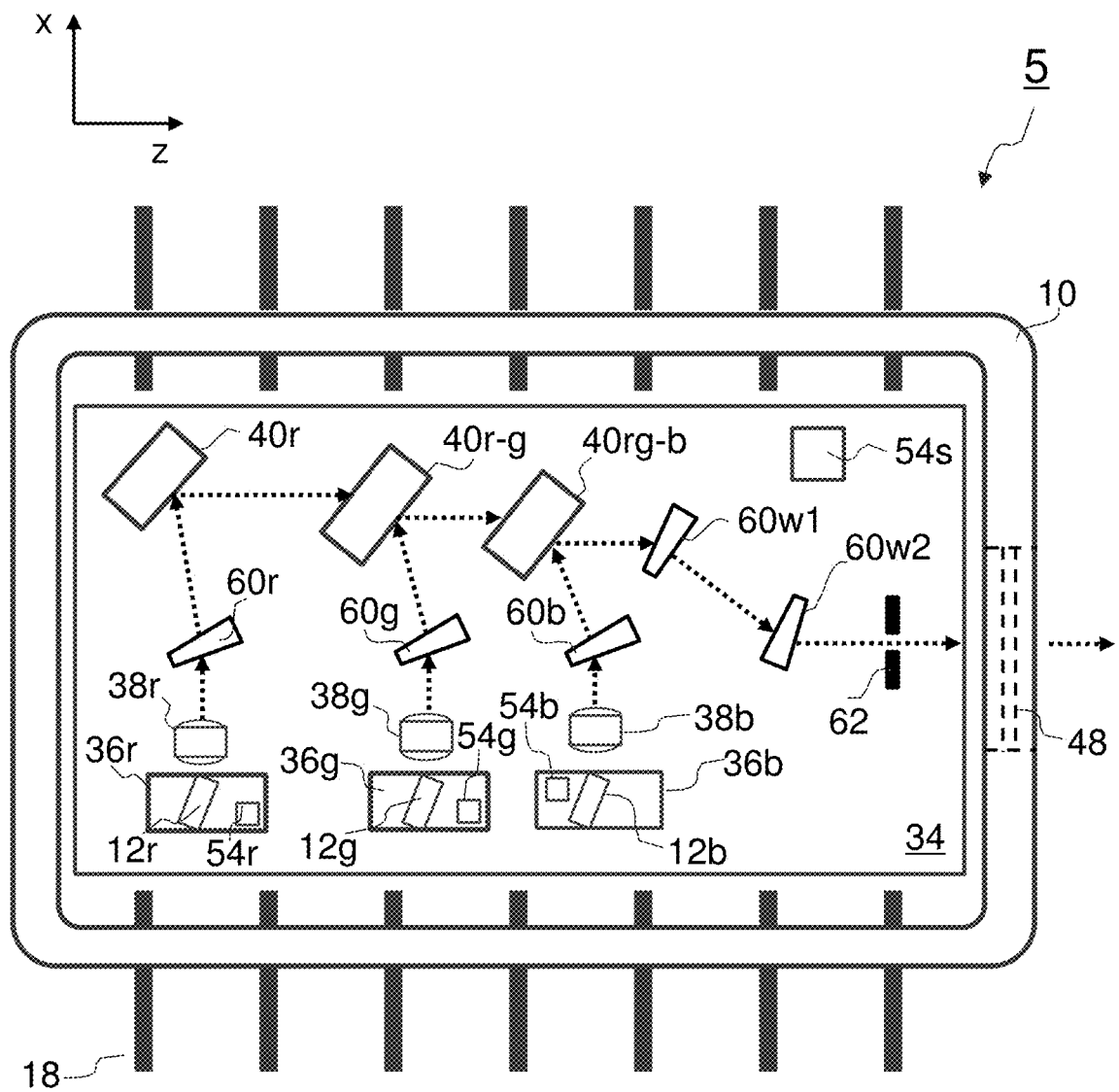
FIG. 10 is a schematic plan view of a SLED source module according to a seventh embodiment.

FIG. 10 is a schematic plan view of a source module according to a seventh embodiment which, compared with previous embodiments, additionally incorporates beam-shaping components and a diaphragm. The output coupling is free-space output through a window 48 in the end wall of the housing 10, but it will be understood that a variant with fiber output is also possible. The other components and their general arrangement will be recognized from the previous embodiments, namely a butterfly package 5 with pins 18 accommodates first, second and third SLED sources 12r, 12g and 12b, labelled 'r', 'g' and 'b'. As in the previous embodiments, the SLEDs 12r/g/b are mounted on respective submounts 36r/g/b which are mounted on a main board 34. The SLEDs 12r/g/b have respective temperature sensors 54r/g/b arranged proximal thereto on the submounts 36r/g/b as well as a further temperature sensor 54s being provided on the main board 34. Collimating lenses 38r/g/b are arranged to collimate the divergent output beams from the SLEDs 12r/g/b The SLED sources 12r/g/b and their collimating lenses 38r/g/b are arranged on one side of the enclosure so as to generate collimated beams propagating across the enclosure in the x-direction. As in previous embodiments, a mirror 40r is provided for directing the collimated red beam into the z-direction as well as beam combiners 40r-g and 40rg-b for directing the collimated green and blue beams into the z-direction and combining them with the red beam and the red-and-green beam respectively.

However, in contrast to previous embodiments, additional beam-shaping prism components 60r/g/b are arranged in the respective beam paths between the collimating lenses 38r/g/b and the mirror and combiner elements 40r, 40r-g and 40rg-b. Beam shaping may be important for SLED sources, since SLED sources tend to have a pronounced beam ellipticity due to their specific design rules (e.g., having a relatively high optical confinement in the waveguide to improve electro-optical efficiency, therefore resulting in relatively large vertical far field angles). A beam-shaping prism as provided here acts to transform an elliptical beam into a circular beam by magnifying the elliptical beam in one dimension. The beam-shaping prism for each of the individual SLED beams is schematically illustrated as a single anamorphic prism. As a consequence, the beam is deflected out of the x-direction, so the the mirror and combiner elements 40r, 40r-g and 40rg-b are tilted away from a 45 degree orientation in order that they deflect the beams into the z-direction. However, an anamorphic prism pair could be used instead of a single anamorphic prism in which case the mirror and combiner elements 40r, 40r-g and 40rg-b could be arranged at 45 degrees as in the previous embodiments. The reason why beam-shaping prisms 60r/g/b may be useful is that, after the collimation lenses 38r/g/b the individual beams of the SLEDs may not have the same beam diameter in the horizontal and/or vertical directions (respectively z- and y-directions in the drawings). This is because the light from different SLED sources will not in general be emitted with the same divergence angles; in particular the divergence angle (far-field angles) for the horizontal (slow) axis and vertical (fast) axis are usually quite different, therefore resulting in a larger beam diameter in the vertical direction and a smaller beam diameter in the horizontal direction. Beam-shaping may be needed for certain applications, such as projector or display applications, in order to meet a specification requirement to have the same beam diameters and hence the same divergence angles in both horizontal and vertical direction for all three colors of the color palette, i.e. RGB here for additive mixing, or cyan, magenta and yellow (CMY) for negative mixing.

After the beams have been combined and before the combined beam is output from the module, the combined output beam is fed through an anamorphic prism pair 60w1, 60w2 to provide further beam shaping. With an anamorphic prism pair, it is noted that the prisms can be arranged relative to each other so that the input and output beams are parallel, i.e. have the same propagation direction, but offset from each other. The beam-shaping prisms for the white (combined) beam could also be useful for performing a final adjustment to the ellipticity of the combined beam as might be desirable for display or projector applications, or for imaging applications where a certain beam shape on the object/sample is needed, as is the case for fundus imaging, for example.

An aperture 62 (diaphragm/iris) is arranged prior to the output to clean up the output beam characteristics, for example to remove diffraction artefacts that may have arisen as a result of the collimation lenses or other unwanted effects. The aperture 62 may also serve to block any stray light that is present within the enclosure of the optical module from exiting the optical module. The diameter of the aperture may typically be between about 0.25 mm and 2 mm, for example 0.30 mm, 0.50 mm, 0.75 mm, 1.00 mm, 1.25 mm, 1.50 mm. The aperture could be integrated into the optical window 48 of the module. Further apertures may be provided for other beams, such as for the red, green or blue SLED beams, or for the combined red and green beam. It will be understood that provision of apertures is an independent design choice not linked to provision of beam-shaping optics, so for example any of the previous embodiments could be modified by providing apertures and/or beam-shaping prisms.

It will also be understood that beam-shaping prisms may be provided selectively as needed, e.g. beam shaping may only be needed for one or two of the SLEDs. A beam-shaping prism or prism pair may also be provided for shaping the output beam of a laser diode in the case that the module also includes a laser diode. Beam clean-up using beam-shaping prisms and/or apertures (diaphragms/irises) may be particularly useful when the module is of the type with a free-space output to improve the quality of the output beam, but may also be useful for optical fiber output to improve coupling efficiency into the fiber.

In any of the above embodiments, the beam combiners which receive a light beam on their back faces preferably have antireflection coatings (ARCs) on their back faces. Each ARC will typically be optimized for the incident wavelength range, the incident angle and the incident polarization state of the incident beam. The beam combiners may additionally or instead have integrally formed on their back faces, and/or their front faces, coatings for other purposes such as wavelength-dependent filtering, e.g. an edge filter, and polarization, e.g. linear polarizer.

It will be understood that variants of any of the above embodiments may be realized which exchange the red, green and blue SLEDs with SLEDs in other wavelength ranges that can be fabricated with available semiconductor crystal materials. In the above embodiments, the SLEDs may be based on edge-emitting ridge structures. The principal materials systems of choice are GaAlInN (sometimes referred to as GaN-based or nitride-based), GaAlInP (sometimes referred to as phosphide-based) and GaAlAs (sometimes referred to as arsenide-based). Such modules could be also realized with SLED devices based on the InP material systems for broadband light sources in the wavelength range of 1200 to 1900 nm, for example. For current commercial SLEDs in the visible and near infrared (NIR) ranges, phosphide- and arsenide-based systems are predominantly used for red wavelengths and nitride-based systems for blue and green wavelengths. The wavelength range of each SLED may be, for example, between 3 nm and 30 nm at full width half maximum, i.e. at 3 dB attenuation, in the visible range or between 10 nm and 160 nm in the NIR range.

In the above embodiments, the beam combiners could have any of the following features. The beam combiners could have polarising beam splitter properties in that they behave in a way that depends on the polarization state of the incident light to reflect one polarization (e.g. TE/horizontal) and transmit another (e.g. TM/vertical) or vice versa. The beam combiners may reflect or transmit depending on whether the incident light is above or below a threshold wavelength, such as reflecting shorter wavelengths and transmitting longer wavelengths or vice versa in the manner of a combiner used for wavelength division multiplexing applications. The beam combiners may also be provided with different splitting ratios as desired, e.g. for power balancing and to tap off a portion of the power for power monitoring.

It will be understood that the 3-SLED source embodiments described above can be modified to remove one of the SLEDs to provide corresponding 2-SLED source modules. For example, in the case of the embodiment of FIG. 5, if the "blue" SLED components were removed to make a 2-SLED module, then only one mirror would remain, namely mirror 40g.

While the illustrated embodiments have 3 SLED sources, further embodiments may be implemented with four, five, six or more SLEDs. The SLEDs are preferably arranged on a common substrate 34. The SLEDs are integrated in a common package as described in the above embodiments for 3 SLEDs. With higher numbers of SLEDs, larger packages may be needed, e.g. butterfly packages with more than 18 pins that have more internal volume. Four or more SLEDs may be beneficial for achieving a desired specification, for example to span a wider spectrum than would be possible with three SLEDs, or to combine visible (e.g., RGB) SLED emitters with NIR SLED emitters or LDs to support multiple modes of use (modalities) in a single module. One concrete example, would be to have an optical module accommodating one group of, e.g. 2 or 3, SLEDs for RGB output (e.g., for color fundus imaging) and another group of, e.g. 3, SLEDs for high-resolution (HR) OCT. Another concrete example would be a module with a combined SLED source (e.g. with 3 SLEDs) for HR-OCT in the wavelength range 780-930 nm and a further single SLED source with a center wavelength of around 750 nm for scanning laser ophthalmoscopy (SLO) and/or eye tracking.

Some system applications employing modules as described above are now discussed.

Figure 11:
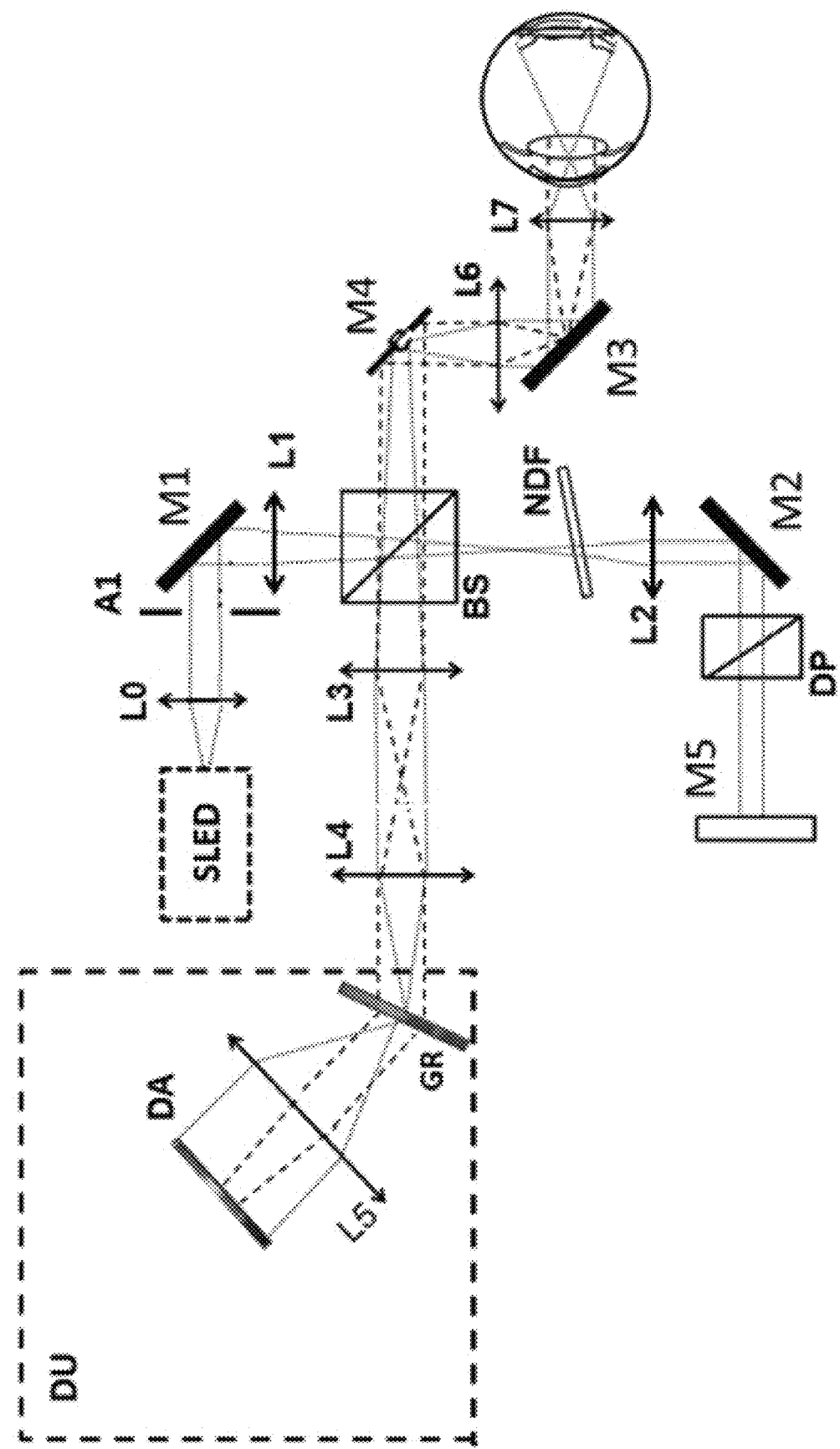
FIG. 11 is a schematic diagram of an example optical coherence tomography (OCT) system which comprises a SLED source module embodying the invention.

FIG. 11 is a schematic drawing of a static-field Fourier-domain OCT system employing a SLED source module as described above to provide illumination over an area of the sample. This is a spectral domain system using the broadband, high-brightness SLED source module and a detector to separate the wavelengths spatially and project them onto a one- or two-dimensional (2d), i.e. array, sensor. The illustrated parts are as follows:

| | |
|---|---|
| SLED | SLED source module |
| A1 | aperture |
| BS | beam splitter |
| L0-L7 | achromatic lenses |
| NDF | neutral density filter |
| M1-M4 | mirrors |
| DP | dispersion prism |
| GR | diffraction grating |
| DU | detector unit |
| DA | detector array |

The SLED source module SLED outputs a circular section beam which passes through circular aperture A1, is reflected 90 degrees by a plane mirror M1 and is then focused by spherical lens L1. A beam splitter BS is arranged to split the light into a first component and a second component. The first component traverses a sample arm by being projected onto a mirror M4. The light is reflected by 90° from the mirror M4. The beam is collimated by lens L6, projected onto mirror M3 and once again focused using lens L7. A human eye is placed with its lens being in an appropriate position, e.g. at the focal position of lens L2 as illustrated. The light which is backscattered from the retina is directed back through the same path until beam splitter BS. At the beam splitter BS the backscattered component interferes with the second component returning from the reference arm. Meanwhile, in the reference arm, the source light after passing for the first time through the beam splitter BS passes through a neutral density filter NDF to adjust the power; after that it is recollimated by cylindrical lens L2 and reflected by 90° using mirror M2. It further passes a dispersion prism DP to compensate for the dispersion in the sample arm. It is reflected by 180° with mirror M5. The reflected beam then goes back through the same path in the reference arm until it reaches the beam splitter BS, where it interferes with the backscattered component from the sample arm. From the beam splitter BS the combined components from the sample and reference arms are projected via lenses L3 and L4 into the detector unit DU. A diffraction grating GR which spatially separates the wavelength components and projects them onto a 2D sensor DA via a collimating lens L5, this 2D setup being suitable in a spectral domain configuration using a broadband source. It will be understood that the illustrated transmission diffraction grating GR could be replaced by a reflection diffraction grating.

It will be understood by those skilled in the art of OCT systems, that a free-space beam splitter BS as illustrated may be substituted with a fused fiber coupler, and the free-space beam paths between the optical elements with optical fiber, in particular single-mode optical fiber, so that the interferometric part of the OCT system, i.e. the four arms around the beam splitter, is implemented in optical fiber and optical fiber components.

We have illustrated a specific static OCT configuration, by way of example only, but the SLED source module is also suitable for other kinds of OCT system. Example OCT systems that may use a SLED source module as described above include: imaging and sensing techniques, where the beam is kept static; imaging and sensing techniques, where the beam is scanned across an object; illumination, where the beam is kept static; and illumination, where the beam is scanned. Scanning devices are, in the context of this disclosure, understood to include methods that move a beam across an object. The beam might also be spatially modulated, e.g. by using digital mirror devices, spatial light modulators or similar.

Figure 12:
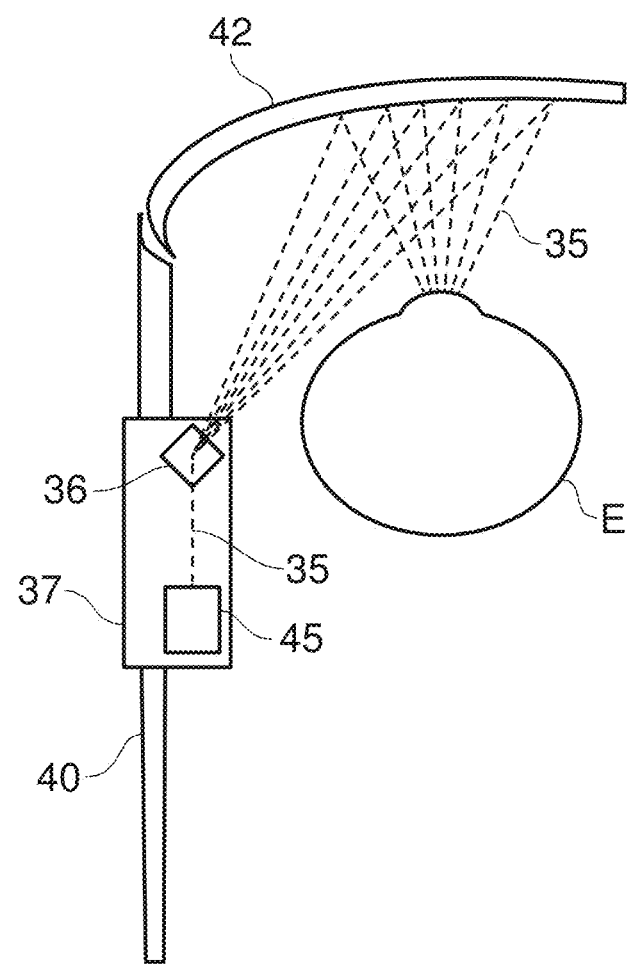
FIG. 12 shows an example direct projection system in a monocle format which comprises an RGB SLED source module embodying the invention.

FIG. 12 shows an example direct projection system in a monocle format, i.e. glasses or spectacles for a single eye. A housing 37 is integrated midway along a temple 40 and houses an RGB SLED module 45 as described above. The combined RGB light beam 35 output by the SLED module 45 is directed to a scanning element 36 which projects an image on the inside surface of a lens 42 which is then reflected onto a wearer's eye E to directly project into the eye. It will be understood that the same basic structure would be suitable for conventional use, where an image is formed on the inside surface of the lens for the wearer to view conventionally. Moreover, it will be understood that the reference to the lens 42 does not imply that the lens 42 has any lensing function insofar as the projection system is concerned, rather it merely serves to provide a reflection surface for direct projection (or projection surface for conventional projection).

Figure 13:
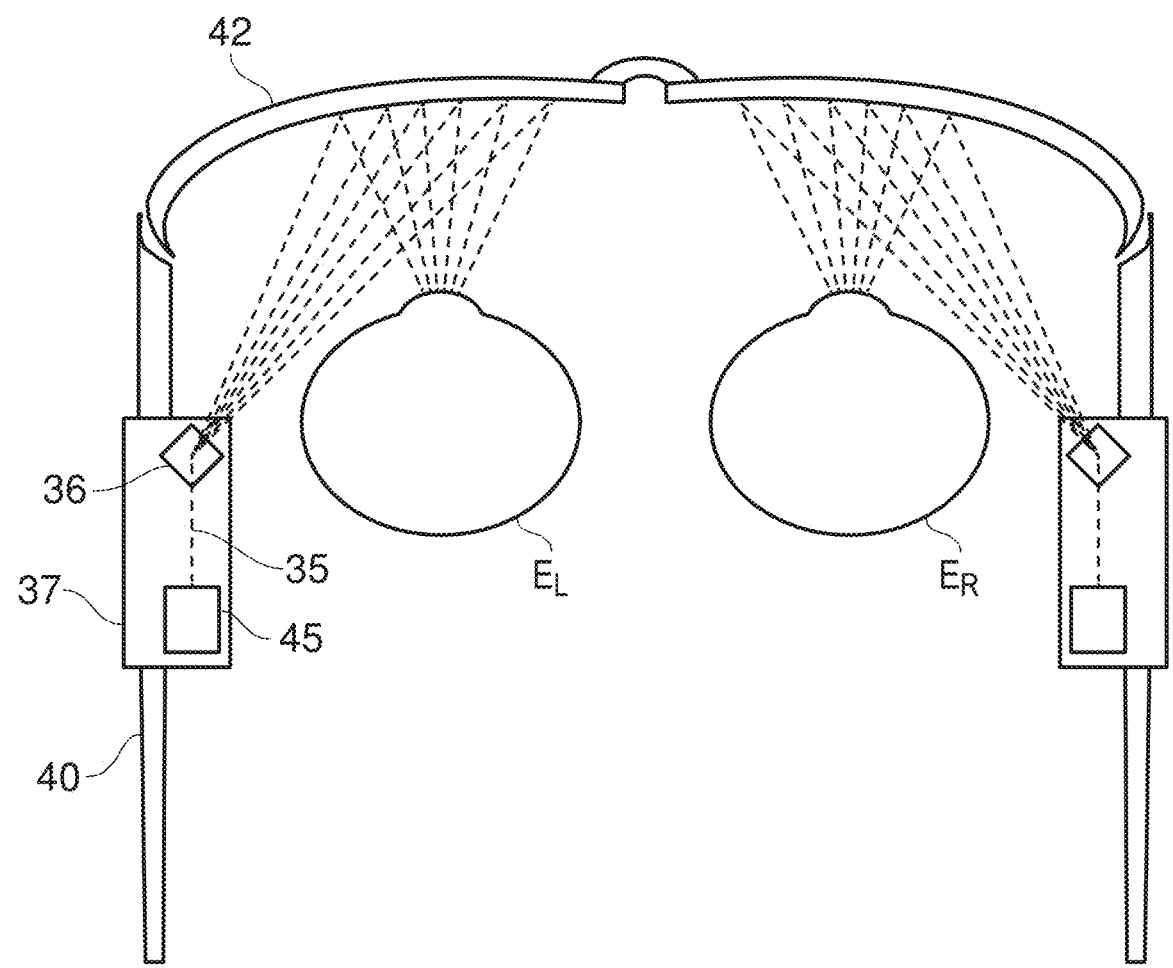
FIG. 13 shows an example direct projection system in a spectacles format which comprises an RGB SLED source module embodying the invention.

FIG. 13 shows an example direct projection system in a spectacles format which is essentially a doubled-up version of the single-eye system of FIG. 12 for direct projection into the left eye EL and right eye ER. The same reference numerals are used. Projection into both eyes allows for additional possibilities, such as stereoscopic imaging for 3D.

Figure 14:
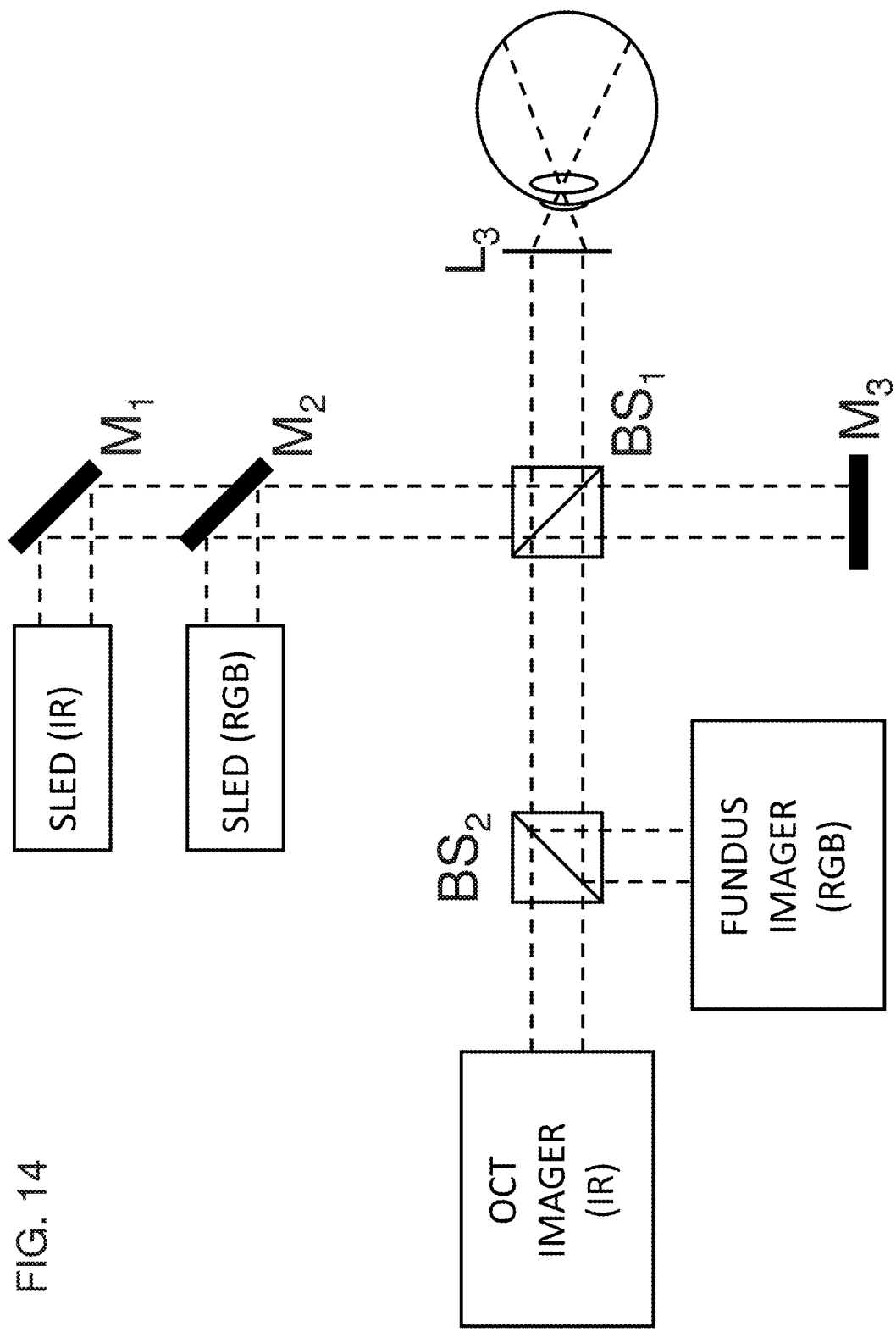
FIG. 14 is a schematic diagram of an example combined OCT and fundus imaging system which comprises two SLED source modules embodying the invention.

FIG. 14 is a schematic drawing of a combined OCT and fundus imaging system for obtaining images of a human or mammalian eye employing two SLED source modules as described above, one with IR output band for OCT imaging and another with a visible (RGB) output band for fundus imaging. The specification of the RGB SLED source module is, for example: a blue SLED with a center wavelength of 455 nm and a 3-dB bandwidth of 10 nm, a green SLED with a center wavelength of 510 nm and a 3-dB bandwidth of 10 nm, and a red SLED with a center wavelength of 650 nm and a 3-dB bandwidth of 10 nm. The specification of the IR output may be met by a single IR SLED, for example a SLED with a center wavelength of 845 nm, 3 dB bandwidth of 145 nm, 10 dB bandwidth of 165 nm, 10 dB wavelength range of 765-930 nm, 10 mW output power and a coherence length of 2.9 micrometers. It will be appreciated this output is from the red end of the visible to near-infrared, which is suitable for OCT systems. The parts shown are as follows:

| | |
|---|---|
| SLED (IR) | IR SLED source module |
| SLED (RGB) | RGB/white-light source module |
| BS1, BS2 | beam splitters |
| L1 | lens |
| M1, M2, M3 | mirrors |

Each SLED module outputs a collimated, circular or elliptical section beam. The collimated beams are reflected 90 degrees by plane mirrors M1 and M2 into a common path, wherein mirror M2 allows the IR SLED beam to pass through it and combine with the RGB SLED beam at the front face of mirror M2. A beam splitter BS1 is arranged to reflect the IR and SLED beam into a path, called the sample arm, that features a focusing lens L1, which focuses the SLED beams onto a desired focal plane on the eye, e.g. cornea, lens, pupil or retina. A certain portion of the IR/RGB light is transmitted at beam splitter BS1 into a separated path, called the reference arm, which incorporates another mirror M3 that reflects the IR/RGB light and that has a path length that is matched to the path length of the sample arm. The light which is backscattered from the eye is directed back through the same path until beam splitter BS1, where the IR light of both sample and reference arm interfere. At the beam splitter BS1 the backscattered component passes through without reflection to a second beam splitter BS2 which allows the IR component of the light to pass through it and be received by an OCT imaging unit and which reflects the RGB component of the light by 90 degrees into a fundus imaging unit. We have illustrated a specific static-field OCT/fundus imaging configuration, by way of example only, but the SLED source module is also suitable for use in a scanning field OCT/fundus system. Example applications of the IR SLED source module include: spectral-domain or Fourier-domain OCT where the beam is focused to a small point of high lateral resolution and scanned in two dimensions across an object; spectral-domain or Fourier-domain line-field OCT imaging where the beam is focused to a narrow line and scanned in one dimension across an object; spectral-domain or Fourier-domain full-field OCT imaging where the beam is kept static and not scanned across an object; spectral-domain or Fourier-domain optical coherence microscopy (OCM) where the beam is focused to a small point or narrow line and scanned across an object. The beam might also be spatially modulated, e.g., by using digital mirror devices, spatial light modulators or similar. It will be understood that either the OCT-specific or the fundus-specific components could be removed from the illustrated system to make a fundus system or an OCT system respectively.

Figure 15:
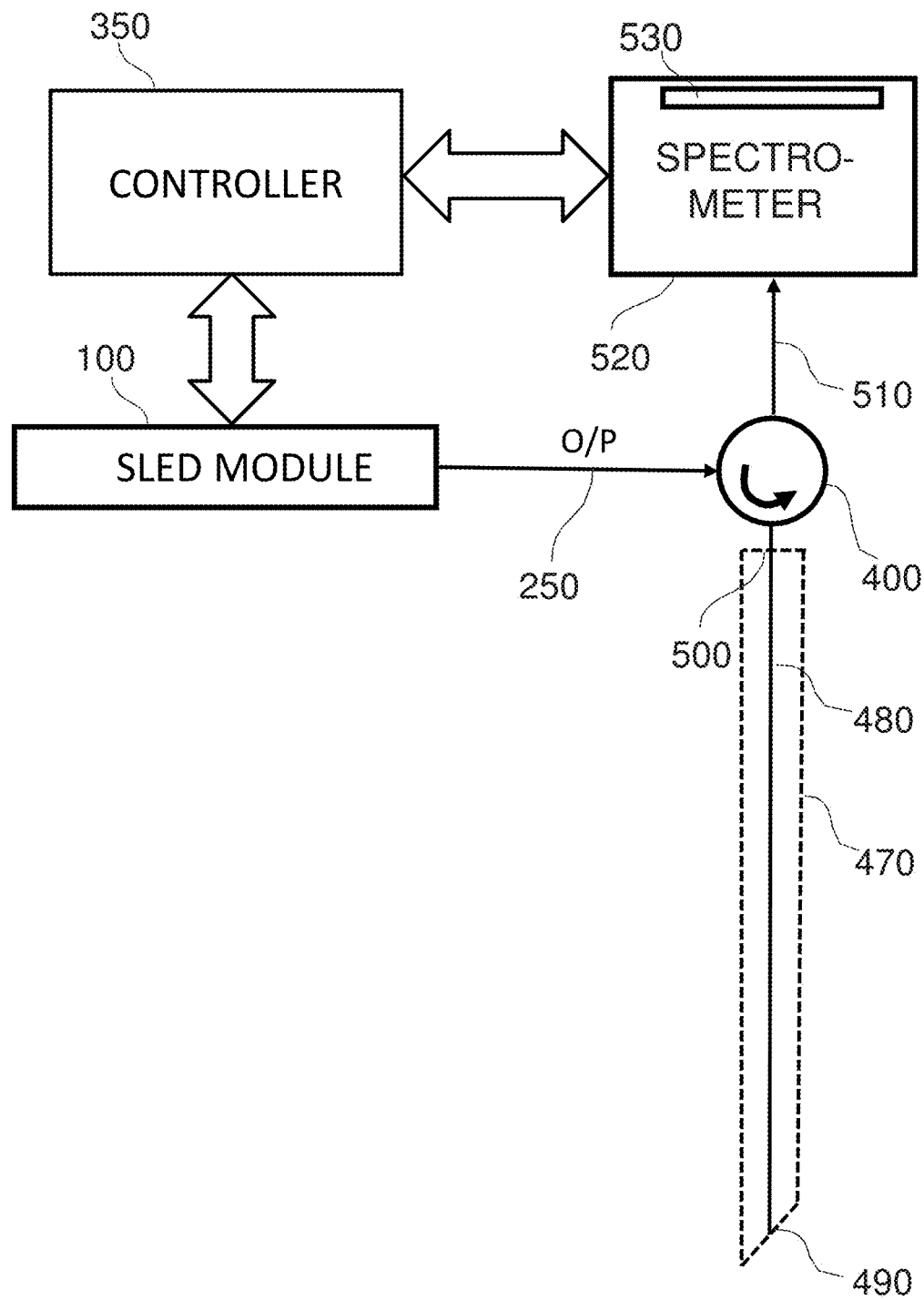
FIG. 15 is a schematic drawing of a medical device system comprising a SLED source module embodying the invention.

FIG. 15 is a schematic drawing of a medical device system comprising a SLED module 100 as described above and downstream optical components that form an endoscopic, laparoscopic, bronchoscopic or catheter-like medical device. An optical path 250 connects the source module 100 and an optical circulator 400. The system further comprises an insertion tube 470, which may be rigid or flexible, suitable for insertion into a patient, for example into a bodily orifice, such as a blood vessel, digestive tract, lung, colon, esophagus etc. The insertion tube 470 includes a light guide 480 which may be formed entirely or in part from an optical fiber or optical fiber bundle, or may be a hollow light guiding tube or some other light guide, and may include free-space optical elements such as lenses, e.g. for collimating, coupling in, coupling out and focusing. The light guide terminates at or near a distal tip 490 of the insertion tube. Light from the source module 100 is supplied to the distal tip 490 via the circulator 400 and any necessary coupling optics (not shown) between the circulator 400 and proximal end 500 of the insertion tube. Light collected from the sample area adjacent the distal tip 490 of the insertion tube 470, e.g. by scattering or fluorescence, may be guided back to the detection optics also by the same light guide 480 that conveyed the excitation light, or via a different light guide (not shown) arranged in the insertion tube 470. The collected light passes through the circulator 400 via a light path 510 to a spectrometer 520 and light detector 530. If no spectral filtering of the collected light signal is needed, then a spectrometer will of course not be present prior to the light detector. The light detector 530 may be an array detector such as a charged coupled device (CCD) or photodiode array, or a light detector without spatial resolution, e.g. a single photodiode. The system is under the control of a controller 350 via control lines schematically illustrated with double-headed arrows which may additionally have data processing functionality, e.g. for image processing or other data analysis of signals received at the detector 530. Alternatively, measurement data may be passed, e.g. by the controller, to a separate computing apparatus for image processing and/or data analysis. Another variation would be to replace the circulator with a fused fiber coupler or free-space coupler. As well as a plurality of SLEDs, the source module 100 may also include a laser diode as in the embodiment of FIG. 9 which can be used for surgical purposes, such as polyp removal.

It will be clear to one skilled in the art that many improvements and modifications can be made to the foregoing exemplary embodiments without departing from the scope of the present disclosure.

What is claimed is:

1. An optical source module comprising: a housing defining an enclosure of free space; first, second and third superluminescent light emitting diode, SLED, sources arranged in the enclosure to emit first, second and third SLED beams having respective first, second and third wavelength ranges, the first, second and third beams propagating in the free space along first, second and third beam paths; a laser diode source arranged in the enclosure to emit a laser beam to propagate in the free space; a first beam combiner arranged in the enclosure to receive the first SLED beam and the second SLED beam, and to combine them into a combined SLED beam with a spectrum including the first and second wavelength ranges and extending in the free space along a combined beam path; a second beam combiner arranged in the enclosure to receive the combined first and second SLED beam and the third SLED beam, and to combine them to form a combined SLED beam with a spectrum including the first, second and third wavelength ranges into the combined beam path; a third beam combiner arranged in the enclosure so that the laser beam is combined with one of the SLED beams so that the laser beam and the SLED beams propagate along the combined beam path; and an optical output port arranged to receive light along the combined beam path and to output the light from the housing.

2. The module of claim 1, wherein the first, second and third wavelength ranges are selected from different ones of red, green and blue visible wavelengths.

3. The module of claim 2, further comprising:
a fourth SLED source arranged in the enclosure to emit a fourth SLED beam having a fourth wavelength range, the fourth beam propagating in the free space along a fourth beam path; and
a fourth beam combiner arranged in the enclosure so that the first to fourth SLED beams are combined to propagate along the combined beam path.

4. The module of claim 3, wherein the fourth wavelength range has a center wavelength at a near-infrared or infrared wavelength.

5. The module of claim 3, wherein the fourth wavelength range has a center wavelength at a visible wavelength.

6. The module of claim 3, further comprising:
a fifth SLED source arranged in the enclosure to emit a fifth SLED beam having a fifth wavelength range with a center wavelength at a near-infrared or infrared wavelength, the fifth beam propagating in the free space along a fifth beam path; and
a fifth beam combiner arranged in the enclosure so that the first to fifth SLED beams are combined to propagate along the combined beam path.

7. The module of claim 6, further comprising:
a sixth SLED source arranged in the enclosure to emit a sixth SLED beam having a sixth wavelength range with a center wavelength at a near-infrared or infrared wavelength, the sixth beam propagating in the free space along a sixth beam path; and
a sixth beam combiner arranged in the enclosure so that the first to sixth SLED beams are combined to propagate along the combined beam path.

8. The module of claim 1, further comprising:
a further laser diode source arranged in the enclosure to emit a further laser beam to propagate in the free space; and
a further beam combiner arranged in the enclosure so that the further laser beam is combined with one of the SLED beams or the laser beam so that the further laser beam, the laser beam and the SLED beams propagate along the combined beam path.

9. The module of claim 1, wherein the first, second and third wavelength ranges have respective center wavelengths at respective near-infrared or infrared wavelengths.

10. The module of claim 9, wherein the spectrum is a continuous spectrum covering the first, second and third wavelength ranges.

11. The module of claim 9, further comprising:
a fourth SLED source arranged in the enclosure to emit a fourth SLED beam having a fourth wavelength range shorter than each of the first to third wavelength ranges and which has a centre wavelength selected to perform at least one of scanning laser ophthalmoscopy and eye tracking; and
a fourth beam combiner arranged in the enclosure so that the first to fourth SLED beams are combined to propagate along the combined beam path.

12. The module of claim 1, wherein the laser beam output by the laser diode source is selected for one of: dye excitation in fluorescence imaging, dye excitation in fluorescence spectroscopy, and eye surgery.

13. The module of claim 1, wherein the first beam combiner comprises a substantially planar optical element having a front side and a back side, the back side being arranged to receive the first SLED beam at a first angle of incidence and route it through the optical element to the front side and output it from the front side from a first position and in a first direction, and the front side being arranged to receive the second SLED beam at a second position that is coincident with the first position and at a second angle of incidence, and to reflect the second SLED beam into a second direction that is coincident with the first direction, and wherein the second combiner comprises a substantially planar further optical element having a front side and a back side, the back side being arranged to receive the combined first and second SLED beam at a further angle of incidence and route it through the further optical element to the front side and output it from the front side from a further position and in a further direction, and the front side being arranged to receive the third SLED beam at a third position that is coincident with the further position and at a third angle of incidence, and to reflect the third SLED beam into a third direction that is coincident with the further direction.

14. The module of claim 1 further comprising:
a first filter arranged after combining the first SLED beam with the second SLED beam and configured to reject wavelength components that are shorter than the second wavelength range; and
a second filter arranged after combining the previously combined first and second SLED beams with the third SLED beam and configured to reject wavelength components that are shorter than the third wavelength range.

15. The module of claim 14, wherein the first filter is additionally configured to reject wavelength components that are longer than the second wavelength range.

16. The module of claim 14, wherein the second filter is a band filter additionally configured to reject wavelength components that are longer than the third wavelength range.

17. The module of claim 14, wherein the first and second filters are band filters additionally configured to reject wavelength components that are longer than the second and third wavelength ranges respectively.

18. The module of claim 14, wherein the first wavelength range covers a wavelength range that is longer than the second wavelength range, which is longer than the third wavelength range.

19. The module of claim 14, wherein the first filter and the first beam combiner are integrated in a first substantially planar optical element having a front side and a back side, the first filter comprising a coating formed on at least one of the front side and the back side of the first substantially planar optical element.

20. The module of claim 14, wherein the second filter and the second beam combiner are integrated in a second substantially planar optical element having a front side and a back side, the second filter comprising a coating formed on at least one of the front side and the back side of the second substantially planar optical element.

21. The module of claim 14 further comprising:
a third filter arranged in the beam path of the first SLED beam before it is combined with the second SLED beam and configured to reject wavelength components that are shorter than the first wavelength range.

22. The module of claim 21, wherein the third filter is additionally configured to reject wavelength components that are longer than the first wavelength range.

23. The module of claim 21, wherein the third filter and the third beam combiner are integrated in a third substantially planar optical element having a front side and a back side, the third filter comprising a coating formed on at least one of the front side and the back side of the third substantially planar optical element.

24. The module of claim 1 further comprising:
a first filter arranged after combining the first SLED beam with the second SLED beam and configured to reject wavelength components that are longer than the second wavelength range; and
a second filter arranged after combining the previously combined first and second SLED beams with the third SLED beam and configured to reject wavelength components that are longer than the third wavelength range.

25. The module of claim 24, wherein the first filter is additionally configured to reject wavelength components that are shorter than the second wavelength range.

26. The module of claim 24, wherein the second filter is a band filter additionally configured to reject wavelength components that are shorter than the third wavelength range.

27. The module of claim 24, wherein the first and second filters are band filters additionally configured to reject wavelength components that are shorter than the second and third wavelength ranges respectively.

28. The module of claim 24, wherein the first wavelength range covers a wavelength range that is shorter than the second wavelength range, which is shorter than the third wavelength range.

29. The module of claim 24, wherein the first filter and the first beam combiner are integrated in a first substantially planar optical element having a front side and a back side, the first filter comprising a coating formed on at least one of the front side and the back side of the first substantially planar optical element.

30. The module of claim 24, wherein the second filter and the second beam combiner are integrated in a second substantially planar optical element having a front side and a back side, the second filter comprising a coating formed on at least one of the front side and the back side of the second substantially planar optical element.

31. The module of claim 24 further comprising:
a third filter arranged in the beam path of the first SLED beam before it is combined with the second SLED beam and configured to reject wavelength components that are longer than the first wavelength range.

32. The module of claim 31, wherein the third filter is additionally configured to reject wavelength components that are shorter than the first wavelength range.

33. The module of claim 31, wherein the third filter and the third beam combiner are integrated in a third substantially planar optical element having a front side and a back side, the third filter comprising a coating formed on at least one of the front side and the back side of the third substantially planar optical element.

34. The module of claim 1, further comprising:
a substrate arranged in the enclosure and having mounted thereon at least the SLED sources, the laser diode source and the beam combiners.

35. The module of claim 1, further comprising:
respective lens components arranged in the enclosure to act on respective individual ones of the SLED beams.

36. An optical source module comprising: a housing defining an enclosure of free space; first, second and third superluminescent light emitting diode, SLED, sources arranged in the enclosure to emit first, second and third SLED beams having respective first, second and third wavelength ranges selected from different ones of red, green and blue visible wavelengths, the first, second and third beams propagating in the free space along first, second and third beam paths; a fourth SLED source arranged in the enclosure to emit a fourth SLED beam having a fourth wavelength range with a center wavelength at a near-infrared or infrared wavelength, the fourth beam propagating in the free space along a fourth beam path; a first beam combiner arranged in the enclosure to receive the first SLED beam and the second SLED beam, and to combine them into a combined SLED beam with a spectrum including the first and second wavelength ranges and extending in the free space along a combined beam path; a second beam combiner arranged in the enclosure to receive the combined first and second SLED beam and the third SLED beam, and to combine them to form a combined SLED beam with a spectrum including the first, second and third wavelength ranges into the combined beam path; a third beam combiner arranged in the enclosure to receive the combined first to third SLED beam and the fourth SLED beam, and to combine them to form a combined SLED beam into the combined beam path.

37. A combined optical coherence tomography and color fundus imaging system comprising an optical source module including: a housing defining an enclosure of free space; first, second and third superluminescent light emitting diode, SLED, sources to provide a source for color fundus imaging arranged in the enclosure to emit first, second and third SLED beams having respective first, second and third wavelength ranges selected from different ones of red, green and blue visible wavelengths, the first, second and third beams propagating in the free space along first, second and third beam paths; at least a fourth SLED source to provide a source for optical coherence tomography arranged in the enclosure to emit a fourth SLED beam having a fourth wavelength range at near-infrared or infrared wavelengths, the fourth beam propagating in the free space along a fourth beam path; a first beam combiner arranged in the enclosure to receive the first SLED beam and the second SLED beam, and to combine them into a combined SLED beam with a spectrum including the first and second wavelength ranges and extending in the free space along a combined beam path; a second beam combiner arranged in the enclosure to receive the combined first and second SLED beam and the third SLED beam, and to combine them to form a combined SLED beam with a spectrum including the first, second and third wavelength ranges into the combined beam path; a third beam combiner arranged in the enclosure to receive the combined first to third SLED beam and the fourth SLED beam, and to combine them to form a combined SLED beam into the combined beam path.

* * * * *